(12) United States Patent
Kibbe

(10) Patent No.: US 10,398,806 B2
(45) Date of Patent: Sep. 3, 2019

(54) TRIPLE BALLOON OCCLUSION AND INFUSION CATHETER FOR FORMING A STENT IN SITU

(71) Applicant: Northwestern University, Evanston, IL (US)

(72) Inventor: Melina R. Kibbe, Chicago, IL (US)

(73) Assignee: Northwestern University, Evanston, IL (US)

( * ) Notice: Subject to any disclaimer, the term of this patent is extended or adjusted under 35 U.S.C. 154(b) by 963 days.

(21) Appl. No.: 13/652,058

(22) Filed: Oct. 15, 2012

(65) Prior Publication Data

US 2013/0053758 A1 Feb. 28, 2013

Related U.S. Application Data

(63) Continuation-in-part of application No. PCT/US2011/032529, filed on Apr. 14, 2011.

(60) Provisional application No. 61/323,953, filed on Apr. 14, 2010.

(51) Int. Cl.
| | |
|---|---|
| *A61L 29/04* | (2006.01) |
| *A61F 2/945* | (2013.01) |
| *A61L 29/14* | (2006.01) |
| *A61L 31/06* | (2006.01) |
| *A61L 31/14* | (2006.01) |
| *A61L 31/16* | (2006.01) |
| *A61M 25/10* | (2013.01) |

(52) U.S. Cl.
CPC ............. *A61L 29/04* (2013.01); *A61F 2/945* (2013.01); *A61L 29/14* (2013.01); *A61L 31/06* (2013.01); *A61L 31/14* (2013.01); *A61L 31/148* (2013.01); *A61L 31/16* (2013.01); *A61M 25/1011* (2013.01); *A61L 2300/114* (2013.01); *A61L 2300/604* (2013.01); *A61M 2025/1052* (2013.01)

(58) Field of Classification Search
CPC .......... A61F 2/945; A61L 29/14; A61L 31/14; A61L 31/16; A61L 31/06; A61L 29/04; A61L 31/148; A61M 25/1011; A61M 2025/1013; A61M 2025/1015; A61M 25/10; C08L 67/00
See application file for complete search history.

(56) References Cited

U.S. PATENT DOCUMENTS

| | | | | |
|---|---|---|---|---|
| 5,411,016 A | * | 5/1995 | Kume et al. ................. | 600/114 |
| 5,419,763 A | * | 5/1995 | Hildebrand .................. | 604/517 |
| 5,514,092 A | * | 5/1996 | Forman et al. ........... | 604/101.03 |
| 5,599,307 A | * | 2/1997 | Bacher et al. ........... | 604/101.05 |
| 5,653,691 A | * | 8/1997 | Rupp et al. .............. | 604/103.06 |
| 5,700,243 A | * | 12/1997 | Narciso, Jr. .............. | 604/102.01 |

(Continued)

OTHER PUBLICATIONS

International Search Report for PCT/US2011/032529 dated Dec. 29, 2011.

(Continued)

*Primary Examiner* — Phong Son H Dang

(74) *Attorney, Agent, or Firm* — Quarles & Brady LLP; M. Scott McBride

(57) ABSTRACT

Disclosed are balloon catheters for forming liquid cast biodegradable arterial stents, typically, the balloon catheters include multiple balloons and multiple ports and include an element for promoting or initiating curing of a polymer solution via polymerization or cross-linking.

12 Claims, 11 Drawing Sheets

(56) References Cited

U.S. PATENT DOCUMENTS

| | | | |
|---|---|---|---|
| 5,885,258 A * | 3/1999 | Sachdeva et al. | 604/530 |
| 5,951,514 A * | 9/1999 | Sahota | 604/101.05 |
| 6,165,196 A * | 12/2000 | Stack et al. | 606/194 |
| 6,409,747 B1 * | 6/2002 | Gobin et al. | 607/113 |
| 6,544,222 B1 * | 4/2003 | Yang | 604/103.01 |
| 6,726,712 B1 * | 4/2004 | Raeder-Devens et al. | 623/1.11 |
| 6,773,452 B2 * | 8/2004 | Shaker | 600/587 |
| 7,648,515 B2 * | 1/2010 | Heinrich et al. | 606/153 |
| 2004/0230316 A1 * | 11/2004 | Cioanta et al. | 623/23.66 |
| 2005/0015046 A1 * | 1/2005 | Weber et al. | 604/96.01 |
| 2005/0070997 A1 * | 3/2005 | Thornton et al. | 623/1.46 |
| 2005/0187604 A1 * | 8/2005 | Eells et al. | 623/1.13 |
| 2006/0122619 A1 * | 6/2006 | Kablik et al. | 606/88 |
| 2008/0021275 A1 * | 1/2008 | Tearney et al. | 600/115 |
| 2008/0132916 A1 * | 6/2008 | Mueller et al. | 606/139 |
| 2010/0036476 A1 | 2/2010 | Guillermo et al. | |
| 2010/0076162 A1 | 3/2010 | Guillermo et al. | |
| 2010/0119833 A1 * | 5/2010 | Madsen et al. | 428/413 |
| 2010/0286531 A1 * | 11/2010 | Ryan et al. | 600/478 |
| 2011/0152683 A1 * | 6/2011 | Gerrans et al. | 600/435 |
| 2011/0218494 A1 * | 9/2011 | Gerrans et al. | 604/101.05 |
| 2012/0259401 A1 * | 10/2012 | Gerrans et al. | 623/1.11 |
| 2013/0123664 A1 * | 5/2013 | Lin et al. | 600/585 |

OTHER PUBLICATIONS

Written Opinion for PCT/US2011/032529 dated Dec. 29, 2011.
International Preliminary Report on Patentability for PCT/US2011/032529 dated Oct. 26, 2012.

* cited by examiner

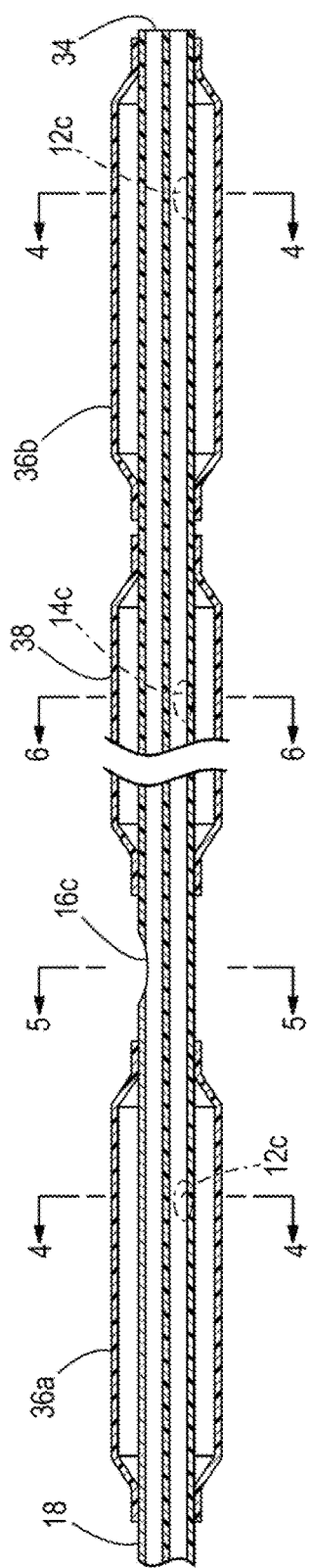
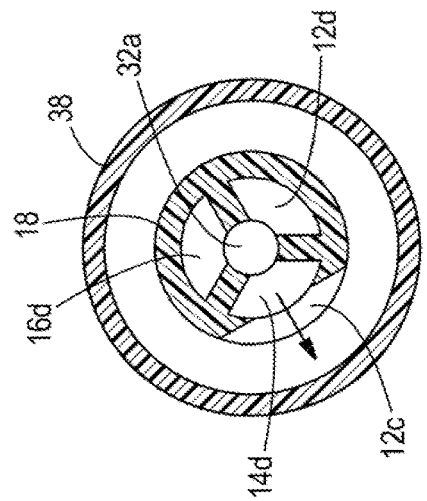
FIG. 4
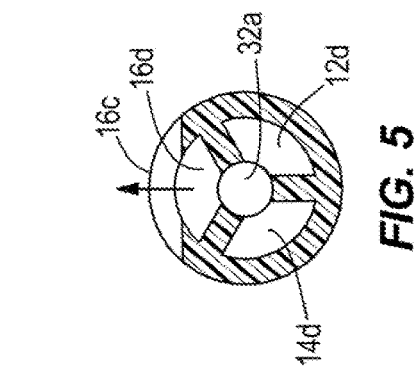
FIG. 5
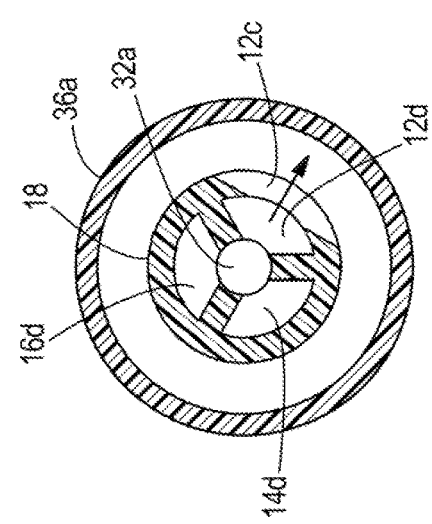
FIG. 6
FIG. 10

TRIPLE BALLOON OCCLUSION AND INFUSION CATHETER FOR FORMING A STENT IN SITU

CROSS REFERENCE TO RELATED APPLICATION

The present application is a continuation-in-part application of International Application PCT/US2011/032529, filed Apr. 14, 2011, which International Application was published on Mar. 15, 2012, as International Publication WO2011/130536. The International Application claims priority of U.S. Provisional Application No. 61/323,953, filed Apr. 14, 2010, the contents of which are incorporated herein by reference in their entireties.

FIELD

The field of the invention relates to catheters and their use for forming arterial stents. In particular, the field of the invention relates to balloon occlusion and infusion catheters for forming liquid cast biodegradable arterial stents.

BACKGROUND

In 2004, more than 1 million Americans underwent coronary angioplasty and more than 80% of these patients received an arterial stent [1]. While stent technology has improved over the years, including the development of drug-eluting stents, failure rates remain high. The high failure rate of current stent technology is secondary to the development of neointimal hyperplasia and acute arterial thrombosis. Neointimal hyperplasia develops from the exaggerated growth of vascular smooth muscle cells (VSMC) which re-occludes the lumen of the artery. Two FDA-approved drug-eluting stents using sirulimus or paclitaxel were designed to prevent this process. However, recent data have shown that drug-eluting stents are associated with higher rates of in-stent thrombosis secondary to a lack of re-endothelialization at the site of intervention. Pre-formed biodegradable stents may address some of these concerns, yet several challenges must be overcome before pre-formed biodegradable stents will be used clinically-including providing sufficient external radial force, compressibility, and elastic recoil, as well as be developed into a low profile delivery system typically no more than a few millimeters in maximum diameter. Liquid cast biodegradable arterial stents are described in the U.S. Provisional Patent Application No. 61/323,955, filed on Apr. 14, 2010, and a U.S. Utility Application filed concurrently herewith and entitled "Liquid cast Biodegradable Arterial Stents," (inventors Melina R. Kibbe and Guillermo A. Ameer, serial, number of the application yet to be assigned). Catheters for forming the liquid cast biodegradable arterial stents disclosed therein and herein are desirable.

SUMMARY

Disclosed are catheters and their use for forming liquid cast biodegradable arterial stents. Typically, the disclosed catheters are multiple balloon occlusion and infusion/aspiration catheters.

The disclosed catheters typically include the following components: (a) a catheter shaft comprising a proximal end and a distal end; (b) a proximal occlusion balloon; (c) a distal occlusion balloon; (d)(1) an inflation lumen in fluid communication with the proximal occlusion balloon and the proximal end of the catheter shaft and (2) an inflation lumen in fluid communication with the distal occlusion balloon and the proximal end of the catheter shaft, wherein the proximal occlusion balloon and distal occlusion balloon when inflated define an interior space within an artery between the inflated proximal occlusion balloon and the inflated distal occlusion balloon; (e) a middle balloon between the proximal occlusion balloon and the distal occlusion balloon; (f) an inflation lumen in fluid communication with the middle balloon and the proximal end of the catheter shaft; (g) at least one irrigation (i.e., infusion)/aspiration port between the proximal occlusion balloon and the distal occlusion balloon and an irrigation/aspiration lumen for delivering/removing a liquid to or from the irrigation/aspiration port, the at least one delivery lumen for delivering a liquid in fluid communication with the proximal end of the catheter shaft; (h) an element, that when activated promotes or initiates curing of a polymer solution of a solution (e.g., via polymerization or cross-linking), where the solution is administered in the interior space within the artery between the inflated proximal occlusion balloon and the inflated distal, occlusion balloon; and optionally (i) a switch for activating element (h). Suitable elements for component (h) may include elements for delivering light such as UV light or visible light which promote or initiate curing of the solution (e.g., via polymerization or cross-linking), where the solution is administered in the interior space within the artery between the inflated proximal occlusion balloon and the inflated distal occlusion balloon. Elements for delivering light may include fiber optic elements, laser elements, and light emitting diode (LED) elements. Other suitable elements for component (h) may include elements for delivering heat, which promotes or initiates curing of the solution (e.g., via polymerization or cross-linking), where the solution is administered in the interior space within the artery between the inflated proximal occlusion balloon and the inflated distal occlusion balloon.

In some embodiments, components (d)(1) and (d)(2) (i.e., m inflation lumen in fluid communication with the proximal occlusion balloon and the proximal end of the catheter shaft and an inflation lumen in fluid communication with the distal occlusion balloon and the proximal end of the catheter shaft, respectively) may comprise or consist of separate inflation lumens that can be utilized to separately inflate the proximal occlusion balloon or the distal occlusion balloon. In other embodiments, components (d)(1) and (d)(2) may comprise or consist of a single lumen in fluid communication with the proximal end of the catheter shaft and both of the proximal occlusion balloon and the distal occlusion balloon such that the single lumen can be utilized to inflate both of the proximal occlusion balloon and the distal occlusion balloon substantially simultaneously.

In operation, the catheter may be inserted into a patient's artery and positioned at an area of interest. Next the proximal occlusion balloon and the distal occlusion balloon are inflated, either substantially simultaneously or in either order, for example, if the catheter comprises separate inflation lumens for the proximal occlusion balloon and the distal occlusion balloon. Next, any fluid in the interior space within the artery between the inflated proximal occlusion balloon and the inflated distal occlusion balloon may be aspirated via component (g) (i.e., at least one irrigation (i.e., infusion/aspiration port between the proximal occlusion balloon and the distal occlusion balloon and an irrigation/ aspiration lumen for delivering/removing a liquid to or from the irrigation/aspiration port). Optionally, the interior space within the artery between the inflated proximal occlusion balloon and the inflated distal occlusion balloon may be washed by infusing and aspirating a wash fluid such as buffered saline. Next, component (g) may be utilized to infuse a polymer or prepolymer solution to the interior space within the artery between the inflated proximal occlusion balloon and the inflated distal occlusion balloon. Next, the middle balloon may be inflated to create a desired thickness for a prepared stent. Subsequently; element (h) may be activated to initiate curing of the polymer or prepolymer solution (e.g., via polymerization and/or cross-linking). Alter polymerization, the middle balloon is deflated. Optionally, the interior space within the artery between the inflated proximal occlusion balloon and the inflated distal occlusion balloon may be washed by infusing and aspirating a wash fluid such as buffered saline (e.g., to remove any non-polymerized and/or non-cross-linked solution). Finally, the distal occlusion balloon and the proximal occlusion balloon axe deflated, and the catheter is removed from the patient's artery.

The catheter comprises at least one irrigation (i.e., infusion)/aspiration port. In some embodiments, the catheter comprises at least one separate irrigation port and at least one separate aspiration port.

The catheter comprises an element that can be activated to promote or initiate curing of a polymer solution via polymerization and/or crosslinking). The element may be positioned within a lumen within the catheter shaft. In some embodiments, the element is an element for delivering light to the interior space within an artery between the inflated proximal occlusion balloon and the inflated distal occlusion balloon (e.g. a fiber optic element that delivers light to the interior space, such as UV light or visible light), in particular, the element may deliver light having a wavelength within a range of 300-500 nm to the interior space (e.g., blue light having a wavelength of about 440-475, 450-475 nm, or 460-475 nm). The element may have a power output of at least about 0.5, 1, 2, 3, 4, 5, 6, 7, 8, 9, or 10 watts, and in some embodiments, the element may have a power output of 0.5-10 watts, 1-6 watts, or 2-5 watts. Preferably, the element may deliver light having an intensity of at least about 10 mW/cm$^2$ (more preferably at least about 20, 30, or 40 mW/cm$^2$). In other embodiments, the element is a heating element for delivering heat to the interior space within an artery between the inflated proximal occlusion balloon and the inflated distal occlusion balloon (e.g., a heating element that delivers sufficient heat to heat the interior space to about 37-50° C. (e.g., 40° C.) in preferably no more than about 10 minutes (more preferably no more than about 5, 4, 3, 2, or 1 minute). In further embodiments, the element is an element that delivers both light and heat to the interior space within an artery between the inflated proximal occlusion balloon and the inflated distal occlusion balloon.

Components of the catheter may be formed from transparent, translucent, or opaque materials. For example, the catheter shaft or inflatable balloons may be formed from transparent, translucent, or opaque material. In some embodiments of the disclosed catheters where component (h) is an element for delivering light to the interior space within an artery between the inflated proximal occlusion balloon and the inflated distal occlusion balloon, the catheter shaft may be transparent or at least translucent within at least a portion of the region between the proximal occlusion balloon and the distal occlusion balloon. Where the catheter shaft is transparent or at least translucent within at least a portion of the region between the proximal occlusion balloon and the distal occlusion balloon, the element for delivering light can be present or inserted within a lumen of the catheter shaft and may deliver light through the catheter shaft at the transparent or translucent portion in order to promote or initiate curing of a polymer solution present in the interior space within an artery between the inflated proximal occlusion balloon and the inflated distal occlusion balloon (e.g., via polymerization and/or cross-linking). Optionally, in some embodiments of the disclosed catheters where component (h) is an element for delivering light to the interior space within an artery between the inflated proximal occlusion balloon and the inflated distal occlusion balloon, the middle balloon may be formed from a transparent or translucent material to facilitate transmittance of light from the element, through the middle balloon, and to a polymer or prepolymer solution present in the interior space within an artery between the inflated proximal occlusion balloon and the inflated distal occlusion balloon.

Preferably, the catheter may be utilized to form a stent that does not include downwardly turned edges. For example, preferably the catheter may be utilized to form a stent that does not include downwardly turned edges abutting the proximal occlusion balloon or tire distal occlusion balloon. In some embodiments of the disclosed catheters where element (h) is an element for delivering light to the interior space within an artery between the inflated proximal occlusion balloon and the inflated distal occlusion balloon, and where the catheter shaft is transparent or translucent within at least a portion of the region between the proximal occlusion balloon and the distal occlusion balloon, the transparent or translucent region be defined by distal and proximal opaque bands that inhibit transmission of light from element (h) to a polymer or prepolymer solution in the interior space. When inflated, preferably the middle balloon overlaps the opaque bands. As such, the catheter may be utilized to prepare a stent that does not include downwardly turned edges.

Optionally, the disclosed catheters, may include an additional component (j) which includes a guide wire and a guide wire lumen extending from the distal end of the catheter shaft to a terminus within the catheter shaft, the terminus being proximal to the irrigation/aspiration port and defining an opening proximal the terminus for the guide wire to exit the catheter shaft. Component (j) may be utilized to guide the catheter to an area of interest within a patient's artery for creating a liquid cast biodegradable arterial stent as disclosed herein. Optionally, the catheter further comprises at least one port through the catheter shaft to the guide wire lumen that permits blood to flow through the guide wire lumen. For example, the catheter may permit blood to perfuse through the catheter when the proximal occlusion balloon and the distal occlusion balloon are inflated.

BRIEF DESCRIPTION OF THE DRAWINGS

FIG. 4 illustrates that poly(1,8 octanediol-co-citric acid) ("POC") forms a stent from liquid phase. A) 3 mm tubing; B) insertion of catheter into tubing; C) injection of POC into tubing; D) polymerization of POC using UV light; E) removal of catheter; and F) Removal of POC cast from the silicone tube revealing a cylindrical stent.

FIG. 5 illustrates a photo of a POC-coated artery after polymerization via UV light.

FIG. 6 illustrates a photo of a POC formed stent from a liquid phase via polymerization by heat.

FIG. 10 illustrates further cross-sectional, views of a shaft of a catheter and inflatable balloons as contemplated herein.

DETAILED DESCRIPTION

Figure 1:
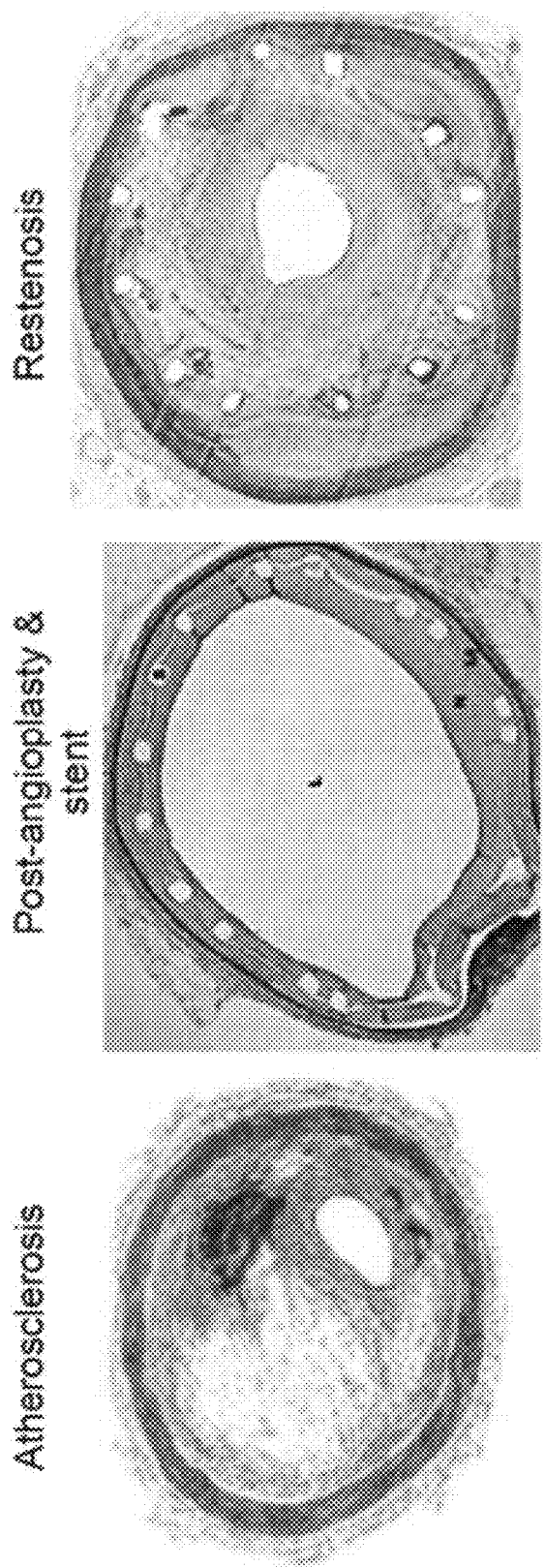
FIG. 1 illustrates development of restenosis from neointimal hyperplasia following balloon angioplasty and stent placement.

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean pins or minus ≤10% of the particular term.

As used herein, the terms "include" and "including" have the same meaning as the terms "comprise" and "comprising."

The presently disclosed catheters may be utilized to treat a patient in need thereof. The terms "patient" and "subject" may be used interchangeably herein. A patient may be a human patient.

A "patient in need thereof" may refer to a patient having or at risk for acquiring an arterial disease or disorder such as atherosclerosis. A patient in need thereof may refer to a patient having or at risk for acquiring neointimai hyperplasia or acute arterial thrombosis. A patient in need thereof may refer to a patient having recently undergone an angioplasty procedure.

The presently disclosed catheters may be used to form liquid cast biodegradable arterial stents. As used herein, "biodegradable" describes a material, such as a polymer, that is capable of being degraded in a physiological environment into smaller basic components. Preferably, the smaller basic components are innocuous. For example, an biodegradable polymer may be degraded into basic components that include, but are not limited to, water, carbon dioxide, sugars, organic acids (e.g., tricarboxylic or amino acids), and alcohols (e.g., glycerol or polyethylene glycol). Biodegradable materials (including polymers) that may be delivered by the triple balloon occlusion catheters contemplated herein in order to prepare the stents contemplated herein may include biodegradable materials disclosed in U.S. Pat. Nos. 7,470, 283; 7,390,333; 7,128,755; 7,094,260; 6,830,747; 6,709,452; 6,699,272; 6,527,801; 5,980,551; 5,788,979; 5,766,710; 5,670,161; and 5,443,458; and U.S. Published Application Nos. 20090319041; 20090299465; 20090232863; 20090192588; 20090182415; 20090182404; 20090171455; 20090149568; 20090117039; 20090110713; 20090105352; 20090082853; 20090081270; 20090004243; 20080249633; 20080243240; 20080233169; 20080233168; 20080220048; 20080154351; 20080152690; 20080119927; 20080103583; 20080091262; 20080071357; 20080069858; 20080051880; 20080008735; 20070298066; 20070288088; 20070287987; 20070281117; 20070275033; 20070264307; 20070237803; 20070224247; 20070224244; 20070224234; 20070219626; 20070203564; 20070196423; 20070141100; 20070129793; 20070129790; 20070123973; 20070106371; 20070050018; 20070043434; 20070043433; 20070014831; 20070005130; 20060287710; 20060286138; 20060264531; 20060198868; 20060193892; 20060147491; 20060051394; 20060018948; 20060009839; 20060002979; 20050283224; 20050278015; 20050267565; 20050232971; 20050177246; 20050169968; 20050019404; 20050010280; 20040260386; 20040230316; 20030153972; 20030153971; 20030144730; 20030118692; 20030109647; 20030105518; 20030105245; 20030097173; 20030045924; 20030027940; 20020183830; 20020143388; 20020082610; and 0020019661; the contents of which are incorporated by reference in their entireties.

Suitable biodegradable polymers that may be utilized to prepare stents via the catheters disclosed herein may include those disclosed in U.S. Published Application No. 20100076162, the content of which is incorporated herein by reference in its entirety. Suitable prepolymers for forming the polymers contemplated herein, may be formed from carboxylic acids and alkane diol precursors. For example, prepolymers may be formed from tricarboxylic acids, such as citric acid, and alkane diols, such as alkane diols having the formula OH—$(CH_2)_n$—OH where n is 6-14 (e.g., 1,8-octanediol). Polymers contemplated herein may be formed from prepolymers such as poly(1,8 octanediol-co-citric acid) (aka "POC"), poly(1,10-Decanediol-Co-Citric Acid) (aka "PDC"), and poly(1,12-dodecanediol-co-citric acid) (aka "PDDC") which optionally may be functionalized at one or more positions (e.g., with an amino group or an acrylate group).

The presently disclosed catheters may be used to form liquid cast polymer stents in situ, by subjecting a polymer an/and/or prepolymer solution to light and/or heat (e.g., UV light or visible light) provided by the presently disclosed catheters. Light and/or heat may be utilized to facilitate curing of an administered polymer and/or prepolymer solution (e.g., via polymerization and/or crosslinking of the polymer and/or prepolymer solution). Optionally, the prepolymers may be functionalized at one or more positions. For example, the prepolymers may be functionalized at one or more hydroxyl positions via reacting the prepolymer with a reagent that provides a crosslinkable amine group or a crosslinkable acrylate group. Optionally, the prepolymer solution comprises a crosslinking initiator compound.

The presently disclosed catheters typically include an element for initiating or promoting curing of a prepolymer solution. Suitable elements may include elements that emit UV or visible light. In some embodiments, the catheters may include an element that emits UV light. UV light may include Ultraviolet A, long wave, or black light, abbreviated "UVA" and having a wavelength of 400 nm-315 nm; Near UV light, abbreviated "NUV" and having a wavelength of 400 nm-300 nm; Ultraviolet B or medium wave, abbreviated "UVB" and having a wavelength of 315 nm-280 nm; Middle UV light, abbreviated "MUV" and having a wavelength of 300 nm-200 nm; Ultraviolet C, short wave, or germicidal, abbreviated "UVC" and having a wavelength of 280 nm-100 nm; Far UV light, abbreviated "FUV" and having a wavelength of 200 nm-122 nm; Vacuum UV light, abbreviated "VUV" and having a wavelength of 200 nm-400 nm; Low UV light, abbreviated "LUV" and having a wavelength of 100 nm-88 nm; Super UV light, abbreviated "SUV" and having a wavelength of 150 nm-10 nm; and Extreme UV light, abbreviated "EUV" and having a wavelength of 121 nm-10 nm. In some embodiments, the catheters may include an element that emits visible light. Visible light may include violet light having a wavelength of 380-450 nm; blue light having a wavelength of 450-475 nm; cyan light having a wavelength of 476-495 nm; green light having a wavelength of 495-570 nm; yellow light having a wavelength of 570-590 nm; orange light having a wavelength of 590-620 nm; and red light having a wavelength of 620-750 nm. In some embodiments, the catheter includes an element that emits light having a wavelength between about 300 nm and 500 nm. In particular, the catheter may include an element that emits light having a wavelength associated with blue light (e.g., light having a wavelength between about 450-475 nm).

The presently disclosed catheters may include an element that emits heat. For example, the element may be a heating element for delivering heat to the interior space within an artery between the inflated proximal occlusion balloon and the inflated distal occlusion balloon. The element may deliver sufficient heat to heat the interior space to about 37-50° C. (e.g., 40° C.) in preferably no more than about 10 minutes (more preferably no more than about 5, 4, 3, 2, or 1 minute), in further embodiments, the element is an element that delivers both light and heat to the interior space within an artery between the inflated proximal occlusion balloon and the inflated distal occlusion balloon.

Atherosclerosis

The presently disclosed subject matter relates to atherosclerosis and the use of balloon catheters for treating atherosclerosis or related conditions such as neointimal hyperplasia. Balloon catheters are known in the art, such as those disclosed in U.S. Pat. Nos. 5,554,092 and 4,636,195, the contents of which are incorporated herein by reference in their entireties.

Atherosclerosis is prevalent in all developed nations and is the leading cause of death and disability in the United States. Deaths due to cardiovascular disease account for 2,400 deaths per day, or 871,517 deaths per year, more than the next, five leading causes of death combined [1]. Seventy-nine million Americans currently have cardiovascular disease and it is estimated that this number will increase significantly due to the growth of the aging population [1]. Furthermore, it is estimated that $432 billion per year is spent in the United States on cardiovascular disease, with a significant portion being attributed to the cost of repeat interventions [1]. One of the current therapeutic modalities for severe arterial atherosclerosis, whether it is from coronary or peripheral arterial disease, consists of balloon angioplasty and stenting (See FIG. 1). Unfortunately, the long-term durability of this procedure is limited, due to the development of neointimai hyperplasia, which results from an aggressive growth of the smooth muscle cells that line the arterial wall. For example, approximately 31-46% of balloon angioplasty sites develop angiographic restenosis at 6 months [1, 2]. Arterial stents and new anti-platelet agents have reduced the 1-year angiographic restenosis rate to 27% [3]. By two years, 20% of patients require repeat balloon angioplasty [4]. Drug-eluting stents have slightly reduced the need for re-intervention [5]. However, long-term data is now suggesting equal or higher mortality rates with drug-eluting stents compared to bare-metal stents [5, 6]. Moreover, the recent COURAGE trial reported that 21% of patients who underwent balloon angioplasty and stenting still required subsequent revascularization within a median time of 10 months [7], Thus, neointimai hyperplasia is an alarming problem that causes significant morbidity and mortality. Currently, no effective therapeutic modality exists to prevent the development of neointimal hyperplasia.

Arterial Injury Response and the Development of Neointimal Hyperplasia

The presently disclosed catheters may be utilized to form stents to treat or prevent arterial injury response and the development of neointimai hyperplasia. The response of the artery to balloon injury has been well described by Clowes et al. [8] Balloon inflation, while designed to be therapeutic, actually causes endothelial cell injury, and with extreme inflation the internal elastic lamina is fractured, thereby exposing the underlying VSMC to circulating blood elements. Platelets immediately aggregate and adhere to the site of injury and an inflammatory response follows, with infiltration of macrophages and leukocytes [9, 11]. The platelets, inflammatory cells, and injured VSMC secrete a variety of growth factors and cytokines, such as basic fibroblast growth factor (bFGF), platelet-derived growth factor, endothelin, and angiotensin II, that stimulate the VSMC to proliferate and migrate to the subintima [9, 12-14]. Concurrently, endothelial cell regeneration occurs through the stimulation of bFGF within 24 hours after injury and continues for 6-10 weeks [15]. Lastly, transforming growth factor-β stimulates a marked upregulation in the genes that encode for extracellular matrix proteins, such as procollagen, collagen, and proteoglycans with deposition of matrix [16, 17]. The culmination of all of these events results in a significant accumulation of cells and matrix within the neointima that ultimately re-occludes the vessel.

Role of NO in the Vasculature

The presently disclosed catheters may be utilized to form liquid cast biodegradable arterial stents that release NO. One promising therapeutic strategy to prevent neointimal hyperplasia has centered on the use of NO, a molecule normally produced in endothelial cells that serves to protect the vessel wall. It is a small, diffusible molecule with a very short half-life that is produced from L-arginine by one of three different enzymes, endothelial nitric oxide synthase (eNOS), neuronal nitric oxide synthase (nNOS), or inducible nitric oxide synthase (iNOS). While these isoforms share a number of similarities, they are also clearly distinct. They all require the cofactors NADPH, FAD, FMN, heme, and tetrahydrobiopterin to catalyze the reaction [18]. But, in general, eNOS and nNOS are constitutively expressed enzymes and NO production is regulated predominantly by intracellular Ca2+ fluxes that permit calmodulin binding which activates the enzymes [18]. Vaughn el at, reported that resting endothelial cells in the vasculature constitutively release ~4 pmol/min/mm$^2$, which equals 5.8 nmol/24 hr/mm$^2$ [19]. In contrast to eNOS and nNOS, iNOS is transcriptionally regulated and is not normally produced by most cells. Typically, iNOS expression in response to cellular stress generates ~100-fold more NO than its constitutive counterparts whose roles are involved in physiological regulations [18].

NO has been shown to possess many different vasoprotective properties, including inhibition of platelet aggregation [20], leukocyte adherence [21], VSMC proliferation [22, 23], VSMC migration [23], stimulation of VSMC apoptosis [24], and endothelial cell growth [25]. NO is also a potent vasodilator [26,27]. All of these properties of NO serve to maintain vascular homeostasis by affecting all the key components in the injury response. Hence, the loss of NO secondary to endothelial cell denudation following vascular injury is pivotal to the development of neointimal hyperplasia.

Since the normal source of NO is lost following vascular injury due to denudation of the endothelial cells, if NO were restored at the site of injury, the development of neointimal hyperplasia should be prevented. Indeed, many investigators have shown that supplementation of NO at the she of injury prevents the development of neointimal hyperplasia. These forms of NO-based approaches have included systemic delivery of L-arginine or NO donors, inhalational NO, local application of NO donors, and gene therapy of one of the NOS enzymes [26-38], Previous work by the principal investigator (PI) has shown that PROLI/NO, a short-acting NO donor, inhibited the development of neointimal hyperplasia by 91% when applied to the periadventitial aspect of an injured artery [39]. Furthermore, a NO-releasing nanoparticle gel also effectively inhibited the development of neointimal hyperplasia following arterial injury and stimulated reformation of an intact endothelial cell layer [40]. Using an alternative approach, Fishbein et al. fabricated NO-releasing stainless steel stents and demonstrated that NO release from the stents inhibited neointimal hyperplasia by 50% [41]. These two approaches, i.e. periadventitial application versus luminal delivery, while very different, were both effective. This demonstrates the highly diffusible nature of NO, thereby allowing the NO to permeate throughout all layers of the arterial wall to impart its overall effect. These studies support the highly effective nature of NO at inhibiting neointimal hyperplasia as well as the feasibility of an intralumenal stent-based delivery approach.

Figure 2:
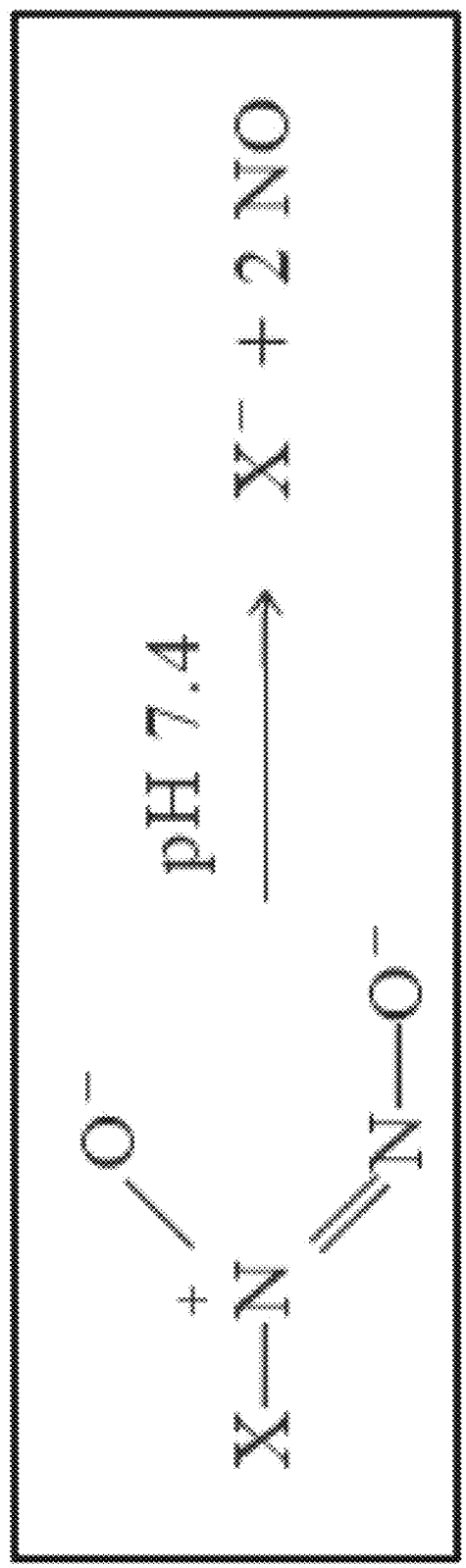
FIG. 2 illustrates diazeniumdiolate dissociation.

Diazeniumdiolate NO donors, often referred to as NONO-ates, are chemical species containing the [N(O)NO]-functional group that have unique characteristics that make them suitable choices for medical applications (FIG. 2). The advantages of diazeniumdiolates over other NO donors include: known predictable rates of NO-release; spontaneity of NO generation; and tunable generation of NO redox forms [42]. The most attractive of these features for medical purposes is that diazeniumdiolate NO donors dissociate spontaneously under physiological conditions (i.e., 37° C., pH 7.4) [42]. They do not require light or other initiators to release NO, just an aqueous environment. Thus, once a diazeniumdiolate is exposed to circulating blood, the hydrogen ions immediately catalyze release of NO that follows first order kinetics. Members of this class of NO donors have been successfully incorporated into synthetic polymeric materials, including biofilms, graft coatings, stent coatings, coatings for oxygen sensors, and extracorporeal circuits [25, 28, 43-38]. All of these approaches have shown extended NO release, varying from days to months, and have demonstrated biologic effects such as inhibition of thrombus formation and VSMC proliferation in vivo or in vitro. Thus, use of NO-based polymeric therapeutics in the vasculature to inhibit the development of neointimai hyperplasia provides a robust tool for the treatment of restenosis.

Drug-Eluting Stents.

The presently disclosed catheters may be utilized to form liquid cast biodegradable arterial stents that release drugs. In an attempt to reduce the high rate of restenosis following balloon angioplasty and stenting, drug-eluting stents were developed. The two FDA-approved drug-eluting stents are Cordis' sirulimus-eluting Cypher stent and Boston Scientific's paclitaxel-eluting Taxus stent. While early data were encouraging and demonstrated reduced rates of restenosis and late lumen loss, late results have recently been disappointing [49]. Several pooled or meta-analysis studies have revealed either similar mortality or worse mortality of these drug-eluting stents compared to bare-metal stents [50, 51], This increased mortality appears to be secondary to an increased rate of in-stent thrombosis [52]. The drug-eluting stents, while inhibiting VSMC proliferation, are also inhibiting endothelial cell proliferation. As a result, the stent is not covered by endothelial cells and remains thrombogenic. Furthermore, Virmani's group recently demonstrated the non-uniformity of healing with drug-eluting stents. The loading dose of the drug varies from strut to strut and the variance in distance between struts exaggerates this heterogeneity, leading to more problems with healing [53]. Therefore, enthusiasm for these two FDA-approved stents has dampened significantly in the past several months and researchers are actively searching for alternatives to combat this problem.

Pre-Formed Biodegradable Stents.

Liquid cast biodegradable arterial stents formed by the presently disclosed catheters have advantageous properties over pre-formed biodegradable stents. The long-term need for stent support following balloon angioplasty has never been demonstrated. Stents are used following angioplasty to prevent elastic recoil. Thus, a stent may be required for only a short duration. Pre-formed biodegradable stents attempt to address this issue. But given that the development of these stents is in its infancy, many challenges remain. The ideal biodegradable stent should include sufficient physical support, acceptable biocompatibility profile, safe degradation characteristics, ease of use, be simple to manufacture and sterilize, and be cost-efficient. With respect to physical characteristics, the stent must have sufficient external radial strength to resist compressive forces, maintain self expandability, have low elastic recoil and be able to anchor itself to the surrounding tissue. In addition, the pre-formed stent must be designed so that it can be collapsed into a delivery device with a small profile (2-3 millimeters). Finally, the delivery device must be flexible in order to negotiate curves during the delivery process. To date, no pre-formed biodegradable stent has been developed that meets all of these criteria.

Figure 3:
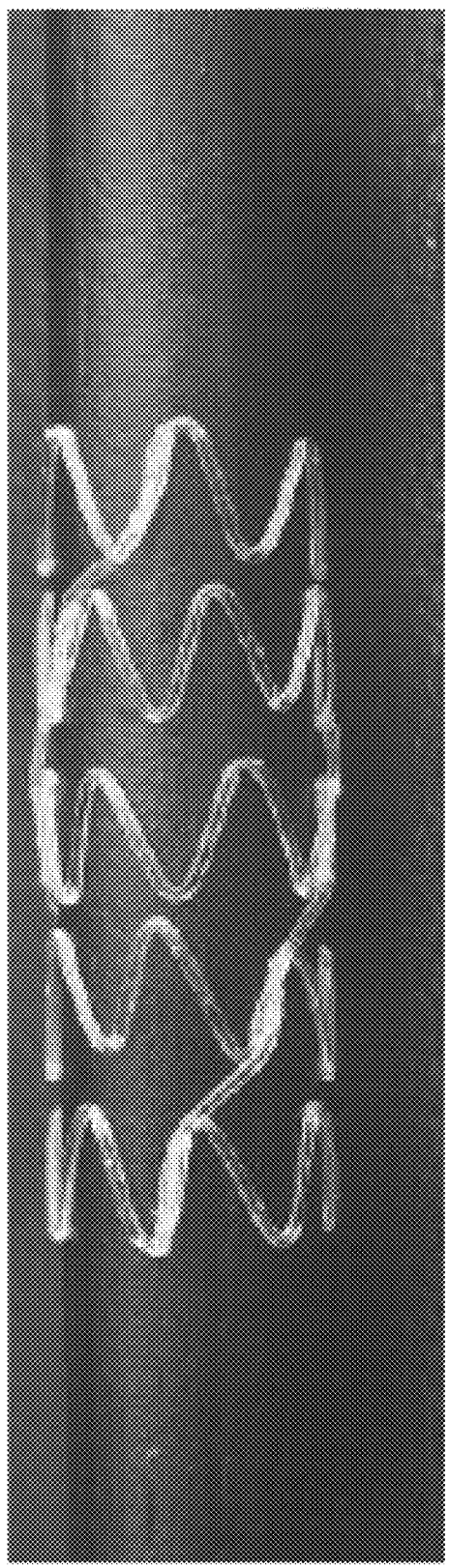
FIG. 3 illustrates an Igaki-Tamai stent, which is a pre-mounted, balloon-expandable poly-L-lactide ("PLLA") stent.

A few biodegradable stents with some of these qualities have been fabricated and placed in humans. The first biodegradable stent was developed at Duke in the early 1980s and was made from woven poly-L-lactic acid (PLLA) polymer strands [54]. However, the first biodegradable stent implanted into humans was the Igaki-Tamai stent, which has a zig-zag helical coil design also made from PLLA (FIG. 3) [55]. Since then, several other investigators have designed stents using polyglycolic acid/poly(lactide-co-glycolide), polycaprolacton, polyhydroxy butyrate valerate, polyorthoester, and polyethyleneoxide/poly(butylene terephtalate), poly(ethylene amide) [56]. Unfortunately, most of these materials induced some degree of inflammation when implanted in animal models [57]. Three other biodegradable stents have shown some promise. These include the polyethylene amide) stent designed by MediVas, the BVS stent fabricated from PLLA by Guidant, and the REVA stent made of a tyrosine-derived polycarbonate material by REVA Medical. These stents must undergo more rigorous evaluation before they can be used. Hence, much work remains to be done before pre-formed biodegradable stents can be used clinically.

Liquid Biodegradable Stents.

The presently disclosed catheters may be utilized to prepare liquid biodegradable stents. The present inventor is unaware of any reports of liquid-formed stents in the literature. Given all of the challenges that pre-formed biodegradable stents face, it is unclear whether preformed biodegradable stents could ever replace bare-metal and drug-eluting stents. What is needed following angioplasty is a material that can provide external radial force to resist recoil, inhibit thrombosis, inhibit neointimal hyperplasia, stimulate re-endothelialization, be biodegradable, thereby allowing for complete healing of the arterial site, and be easy and inexpensive to manufacture, deliver, and use. Also required is a catheter designed to deliver a stent formed from, such material. Disclosed herein are attempts to design and evaluate such a catheter.

The catheters disclosed herein may be utilized to form stents unlike any other stent that has been used in the healthcare arena. The presently disclosed stents are formed in a patient's body from a liquid phase delivered by the disclosed catheters. One suitable prepolymer for forming such stents is POC [58]. POC is a citric acid-based biodegradable elastomeric polymer and has been shown to be biocompatible in vitro and in vivo [58, 59]. A stent formed from this material will polymerize and be cast into the shape of the arterial lumen with the aide of mild heat or light provided by the disclosed catheters. When applied by the presently disclosed catheters, the material will coat the arterial surface at the site of angioplasty, thereby providing strength as well as surface area coverage. The strength of POC can be easily manipulated by varying the degree of acrylation, thereby providing optimal strength and compliance for the vessel. This material may be diazeniumdiolated to spontaneously release a drug, NO, which will inhibit thrombosis as well as the formation, of neointimal hyperplasia while simultaneously stimulating re-endothelialization. Lastly, this material will completely degrade over time, leaving a pristine healthy arterial surface in approximately 6 months. This liquid stent should be easy to fabricate and use and should be very cost-efficient. Therefore, this new technology aims to change the way arterial stenting is approached by dramatically changing the concept of what a stent should be.

To the best of the present inventor's knowledge, disclosed herein are the first attempts to create a stent that forms in the body and is tailored to the patient's individual arterial anatomy. This form of designer medicine is radically different from all other approaches currently utilized in the clinical arena. While biodegradable stents may represent one possible solution to the problems with bare-metal and drug-eluting stents, many challenges exist for the fabrication and delivery of these devices. Disclosed herein are methods to form a stent in situ from a liquid NO-releasing elastomeric polymer. Ideally, the stent will be 1) simple to manufacture, 2) cost-effective, 3) easy to use, 4) biodegradable over time, 5) completely coat the entire arterial surface thereby providing the greatest antithrombotic protection to the artery, 6) offer a high stent-to-artery surface area ratio, thus increasing the area of contact of a drug to the arterial wall (such as NO, which optionally is present in the elastomeric polymer) and increasing the therapeutic effects, and 7) will provide physical characteristics ideal for the vasculature (i.e, compliance, compressibility, elasticity, etc). Also, a benefit of this approach is that compliance of the vessel may be modulated by altering the acrylation of the polymer, which is a significant advance over current technology. This will allow design and development of a stent that has ideal compliance with the native tissue, that resists external compression, and that has sufficient elastic recoil. In fact, one of the shortcomings of preformed biodegradable stents is that they are fabricated with an open ceil matrix design. The presently proposed design with polymeric material limits the compression strength preformed biodegradable stents can achieve. An advantage of the proposed technology is that the entire surface of the artery may be coated, thereby providing greater compression strength to withstand the elastic recoil that occurs following arterial injury. Furthermore, where the stent comprises NO and POC, both the NO and the POC inhibit platelets and stimulate endothelial cell growth. As such, the proposed liquid cast stent, will overcome the shortcomings of current drug-eluting stents. Lastly, because the proposed biocompatible stent will degrade over time, no foreign material will be left in the artery. This concept, i.e. formation of a stent from a liquid material in the body, is a dramatic departure from current therapies and will change current thought about promoting arterial health following vascular interventions. Furthermore, the disclosed approach should have a large impact on the healthcare system, given the broad prevalence of cardiovascular disease.

In order to prepare these liquid cast biodegradable arterial stents, a specialized catheter is required. Tire catheter must be designed to: (1) close-off an arterial area for delivery of a prepolymer solution; (2) aspirate and deliver material such as a prepolymer solution to the closed-off area; and (3) apply light and/or heat to the closed-off area in order to polymerize and/or cross-link the prepolymer solution. Preferably, the catheter is designed to administer a polymerized stent that has smooth edges.

ILLUSTRATIVE EMBODIMENTS

The following examples are illustrative and are not intended to limit the scope of the disclosed or claimed subject matter.

Embodiment 1

A catheter for forming a liquid cast stent, the catheter comprising: (a) a catheter shaft, comprising a proximal end and a distal end; (b) a proximal occlusion balloon; (c) a distal occlusion balloon; (d) an inflation lumen in fluid communication with the proximal occlusion balloon and the proximal end of the catheter shaft and in fluid communication with the distal occlusion balloon and the proximal end of the catheter shaft, wherein the proximal occlusion balloon and distal occlusion balloon when inflated define an interior space within an artery between the inflated proximal occlusion balloon and the inflated distal occlusion balloon; (e) a middle balloon between the proximal occlusion balloon and the distal occlusion balloon; (f) an inflation lumen in fluid communication with the middle balloon and the proximal end of the catheter shaft; (g) at least one infusion/aspiration port between the proximal occlusion balloon and the distal occlusion balloon and an infusion/aspiration lumen for delivering/removing a liquid to or from the infusion/aspiration port, the at least one delivery lumen for delivering a liquid in fluid communication with the proximal end of the catheter shaft; and (h) an element that when activated initiates or promotes curing of a polymer solution administered in the interior space within the artery between the inflated proximal occlusion balloon and the inflated distal occlusion balloon.

Embodiment 2

The catheter of embodiment 1, further comprising: (i) a switch for activating element (h).

Embodiment 3

The catheter of embodiment 1 or 2, wherein element (h) comprises an element for delivering light to the interior space of the artery between the inflated proximal occlusion balloon and the inflated distal occlusion balloon.

Embodiment 4

The catheter of embodiment 3, wherein the element delivers visible light.

Embodiment 5

The catheter of embodiment 3, wherein the element delivers UV light.

Embodiment 6

The catheter of embodiment 3, wherein the element delivers light having a wavelength of about 300-500 nm (e.g., blue light having a wavelength of about 440-475 nm, 450-475 nm, or 460-475 nm).

Embodiment 7

The catheter of any of embodiments 3-6, wherein the element delivers light having an intensity of at least about 10 mW/cm$^2$ (preferably at least about 20, 30, or 40 mW/cm$^2$).

Embodiment 8

The catheter of any of embodiments 3-7, wherein the element is a fiber optic element, a laser element, or a light emitting diode (LED) element.

Embodiment 9

The catheter of any of embodiments 1-8, wherein at least a portion of the catheter shaft is transparent or translucent.

Embodiment 10

The catheter of embodiment 9, wherein the transparent or translucent portion is located between the proximal occlusion balloon and the distal occlusion balloon.

Embodiment 11

The catheter of embodiment 9 or 10, further comprising opaque bands that define a proximal end and a distal end of the transparent or translucent portion.

Embodiment 12

The catheter of embodiment 11, wherein when die middle balloon is inflated, the middle balloon overlaps the opaque bands.

Embodiment 13

The catheter of any of embodiments 1-12, wherein the middle balloon is formed from material that is transparent or translucent and that permits transmission of light from the element to the interior space of the artery between the inflated proximal occlusion balloon and the inflated distal occlusion balloon.

Embodiment 14

The catheter of embodiment 1, wherein the element is a heating element.

Embodiment 15

The catheter of embodiment 14, wherein the element delivers sufficient heat to heat the interior space of the artery between the inflated proximal occlusion balloon and the inflated distal occlusion balloon to about 37-50° C. in no more than about 5 minutes (preferably in no more than about 4, 3, 2, or 1 minute(s)).

Embodiment 16

The catheter of any of embodiments 1-15, wherein component (d) comprises an inflation lumen in fluid communication with the proximal occlusion balloon and the proximal end of the catheter shaft and a separate inflation lumen in fluid communication with the distal occlusion balloon and the proximal end of the catheter shaft, wherein the proximal occlusion balloon and the distal occlusion balloon can be inflated separately.

Embodiment 17

The catheter of any of embodiments 1-15, wherein component (d) consists of a single lumen in fluid communication with the proximal end of the catheter shaft and both of the proximal occlusion balloon and the distal occlusion balloon, wherein the single lumen can be utilized, to inflate both of the proximal occlusion balloon and the distal occlusion balloon.

Embodiment 18

The catheter The catheter of any of embodiments 1-17, comprising at least one separate infusion port and at least one separate aspiration port.

Embodiment 19

A method for forming a liquid cast biodegradable arterial stent, the method comprising: (I) insetting the catheter of The catheter of any of embodiments 1-18 into an artery of a patient in need thereof; (II) inflating the proximal occlusion balloon and the distal occlusion balloon to define an interior space therebetween; (III) delivering a pre-polymer solution into the interior space therebetween; (IV) inflating the inner inflation membrane of the middle balloon; and (V) activating element (h) to cure the pre-polymer solution and form the liquid cast biodegradable arterial stent.

Embodiment 20

The method of embodiment 19, further comprising after step (V) deflating the inner inflation membrane of the middle balloon and aspirating any liquid in the interior space.

EXAMPLE

The following examples are illustrative and are not intended to limit the scope of the disclosed or claimed subject matter.

Example 1

Results

Formation of Stents from Liquid Phase.

To demonstrate the feasibility of forming a solid stent from liquid utilizing catheters as contemplated herein, POC was polymerized into cylindrical structures ex vivo in less than 5 minutes at 40° C. (FIG. 4). Furthermore, FIG. 5 demonstrates the injection of the liquid NO-releasing POC material (50 wt % in water) into 3 mm silicone tubing (simulating an artery), followed by inflation of a 3 mm angioplasty balloon to cast the stem, then polymerization of the stent using UV-VIS (~400 nm) light. FIG. 5F shows the material shaped into the form of a cylindrical stent once the silicone tubing was excised, demonstrating that the NO-releasing material maintains elastic recoil after removal of the tubing. Dye was added to the POC liquid pre-polymer to aid in the visualization of this process.

The inner surface of a harvested porcine artery can be coated with NO-releasing POC to form a stent from liquid material ex vivo. FIG. 6 confirms the ability of the polymer (darker colored) to adhere to the inner wall of the artery, thereby, increasing its resistance to deformation. These studies are proposed to be further investigated as discussed below.

Polymerization.

In order to form a solid stent from liquid utilizing the presently disclosed catheters, polymerization conditions to polymerize the liquid NO-releasing POC material in the least amount of time should be optimized. Tor example, after administering the prepolymer solution to the site of stent formation via the triple balloon occlusion and infusion catheter disclosed herein, polymerization or cross-linking may be initiated by introducing a radical initiator to the prepolymer solution via the catheter disclosed herein. Other investigators have demonstrated the efficacy and safety of in situ radical polymerization of tissue [63-66]. Optionally, polymerization or cross-linking may be initiated or enhanced by heating the prepolymer solution at the site of stent formation via the disclosed catheter. Intravascular devices currently used in patients result in changes to the intravascular temperature. The Rotablator rotational atherectomy device was found to result in temperature increases of 2-4° C. with minimal decelerations but increases of 11-14° C. with continuous ablation or rapid decelerations [67]. The Boston Scientific Cryoplasty Therapy freezes tissue to −10° C. Both of these later devices are FDA approved and are well-tolerated by the surrounding tissue. Optionally, polymerization or cross-linking may be initiated or enhanced by subjecting the prepolymer to light (e.g., UV light) at the site of stent formation via the disclosed catheter. With respect to UV light polymerization, UV light is commonly used to treat a variety of skin pathologies in patients. Thus, damage to the surrounding tissue from either thermal or photo-initiated polymerization is not expected, as the temperatures are in alignment with what is currently used, the polymerization is highly localized to the interface of the vessel, and excess or now-reacted monomers will be aspirated out of the reaction volume. If temperature is used to begin the radical polymerization reaction, initiators that are efficiently activated at 40° C. are commonly available and the disclosed catheter may include a heating element that applies heat to initiate polymerization. If UV-VIS (365 nm) is used, a fiber-optic probe can be inserted within the disclosed catheter and utilized to apply light to initiate polymerization, in both cases, the reaction can be completed within 5 minutes (see Results described herein).

In future work, experiments are proposed: 1) to optimize the conditions for polymerization within 1-2 minutes; and 2) to evaluate and optimize the mechanical characteristics of the polymerized stent for the vasculature. For this aim, w both thermal- and photo-initiated methods to induce polymerization will be evaluated in order to determine the most optimal method for in vivo applications as well as measure and optimize the mechanical properties of the stented artery. As shown herein, POC can be formed into cylindrical bioengineered vascular grafts [68]. These bioengineered grafts were implanted into pigs using the carotid artery bypass model for 7 days and were found to be durable and biocompatible (not shown). Thus, this experiment suggests that POC has characteristics suitable for the vasculature, including sufficient strength to withstand arterial pressure and pulsatility. Different methodologies to induce polymerization of POC into cylindrical casts in situ using both mild heat (~40 C) and UV light will be evaluated. Preliminary data suggest that acrylated POC can be polymerized in a short period of time using UV-VIS light (FIGS. 4 and 5) or temperatures as low as 40° C. (FIG. 6), which should be compatible with in vivo applications. Thus, the POC pre-polymer will be acrylated via the hydroxyl group to allow for radical-initiated thermal or photo polymerization. Various conditions will be modulated to maximize polymerization including degree of acrylation, prepolymer molecular weight, polymer solubility, and polymer viscosity. Parameters that will be assessed include: 1) time to polymerization, 2) polymer tensile strength, 3) polymer elasticity, 4) polymer compliance, and 5) biocompatibility with endothelial cells and VSMC (i.e., effect on apoptosis, migration, and proliferation), ideally, polymerization will be completed within 1-2 minutes with one of these two approaches, as these times are well suited for clinical applications in patients based on the time required, to use other devices commonly in use for treating atherosclerosis.

Polymer Solubility.

The presently disclosed catheters may be utilized to administer and cure a prepolymer solution to an artery. With respect to the solubility of the prepolymer, water-soluble polydiol citrates may be synthesized by using poly(ethylene glycol) and glycerol diacrylate as the diol monomers. However, the use of ethanol/water solutions as a solvent for the pre-polymer also is possible and offers a broader range of pre-polymers (e.g., using as solvent 50:50 ethanol:water). The contact time between the solvent and the "damaged" blood vessel is minimal and the ethanol:water solution would not be expected to cause any major longstanding damage to the artery. However, stent formation will be tested using water or water:ethanol as a solvent for the prepolymer solution for forming the stent. Parameters that will be assessed are the same as described above.

Polymer Viscosity.

The viscosity of the prepolymer utilized by the catheters disclosed herein is on the order of 100 centipose (cp) and a 30 wt % dilution has a viscosity of approximately 10 cp. If needed, the viscosity of the liquid phase can be adjusted with the volume of saline that is used to dissolve the pre-polymer. Initially, a 30 wt % prepolymer solution will be tested.

Stent Formation.

Stents may be cast utilizing the catheters disclosed herein after identifying suitable polymerization conditions. Fresh porcine arteries will be obtained from the local slaughter house (Park Packing Company, Chicago, Ill.). After injection of the NO-POC into the lumen of the artery, the stent will be polymerized with the use of a 4-6 mm angioplasty balloon (to be determined by the diameter of the artery that will be used) and either thermal or photo-initiation, based on the experiments described herein. A thermal radical initiator that is efficiently activated at 40° C. may be utilized. Initiator amounts will be kept to less than 1% of the prepolymer content. The pre-polymer content (in an aqueous solution) typically is about 30 wt %. If photo-initiation will be used, UV-VIS having a wavelength of 365 nm will be utilized. Parameters that will be assessed include; 1) time to complete polymerization, 2) % non-reacted monomers retrieved, 3) % surface area coated, 4) thickness and homogeneity of the stent coating, and 5) attachment strength to the surrounding tissue. Lastly, once the polymer has been formed within the walls of the blood vessel it will be important for the elastomeric and adhesive properties to remain intact to prevent fragmentation and potential loss to the blood stream. As the polymer is a cross-linked network with elastic properties fragments are not expected to form. However, this will be measured as described below. Ideally, 100% surface area coverage in a homogeneous manner will be achieved with less than 10% of monomers being un-reacted and retrieved.

Catheter Development.

In order to deliver the liquid prepolymer to the intravascular space and polymerize it into a solid stent, a specialty catheter is required that can do the following: 1) occlude flow at the desired target site, 2) deliver the liquid polymer or prepolymer solution, 3) be able to initiate curing (e.g., via polymerization and/or cross-linking), 4) be able to cast the polymer into a cylindrical stent shape with desired thickness and no edge effect, and 5) be able to aspirate liquid (e.g., non-reacted monomers or pre-polymers). Thus, the delivery catheter may comprise a double balloon occlusion catheter that has a third, middle balloon that will form the cylindrical cast and further comprises an element for initiating or promoting curing of a prepolymer solution administered at an interior space within an artery between the inflated proximal occlusion balloon and the inflated distal occlusion balloon. This catheter will also be able to aspirate and irrigate the interior space. A prototype of this catheter is shown in FIGS. 7-10.

The shaft of the catheter includes multiple lumens. In total, the balloon catheter may include a shaft having at least four lumens: 1) a lumen (single lumen) or lumens (two separate lumens) in fluid contact with the proximal occlusion balloon and the distal occlusion balloon; 2) a lumen in contact with the middle inflation balloon; 3) an irrigation/aspiration lumen; 4) and a lumen for the element utilized to initiate or promote polymerization (e.g., a lighting element lumen or a heating element lumen).

The shaft of the catheter includes multiple ports for inflating the balloons and/or infusing/aspirating liquid. For example, an infusion/aspiration port or ports may be situated at the inner base of the proximal and distal occlusion balloons and may be used to irrigate the interior space between the inflated proximal and distal occlusion balloons with saline prior to injection of the pre-polymer solution and after polymerization. These ports also may be used to aspirate any non-reacted liquid (e.g., liquid that includes non-reacted monomers or pre-polymer solution), in total, the balloon catheter may include a shaft having at least four ports: 1) proximal balloon occlusion port; 2) a distal balloon occlusion port; 3) a middle balloon inflation port; and 4) an irrigation/aspiration port.

Figure 7:
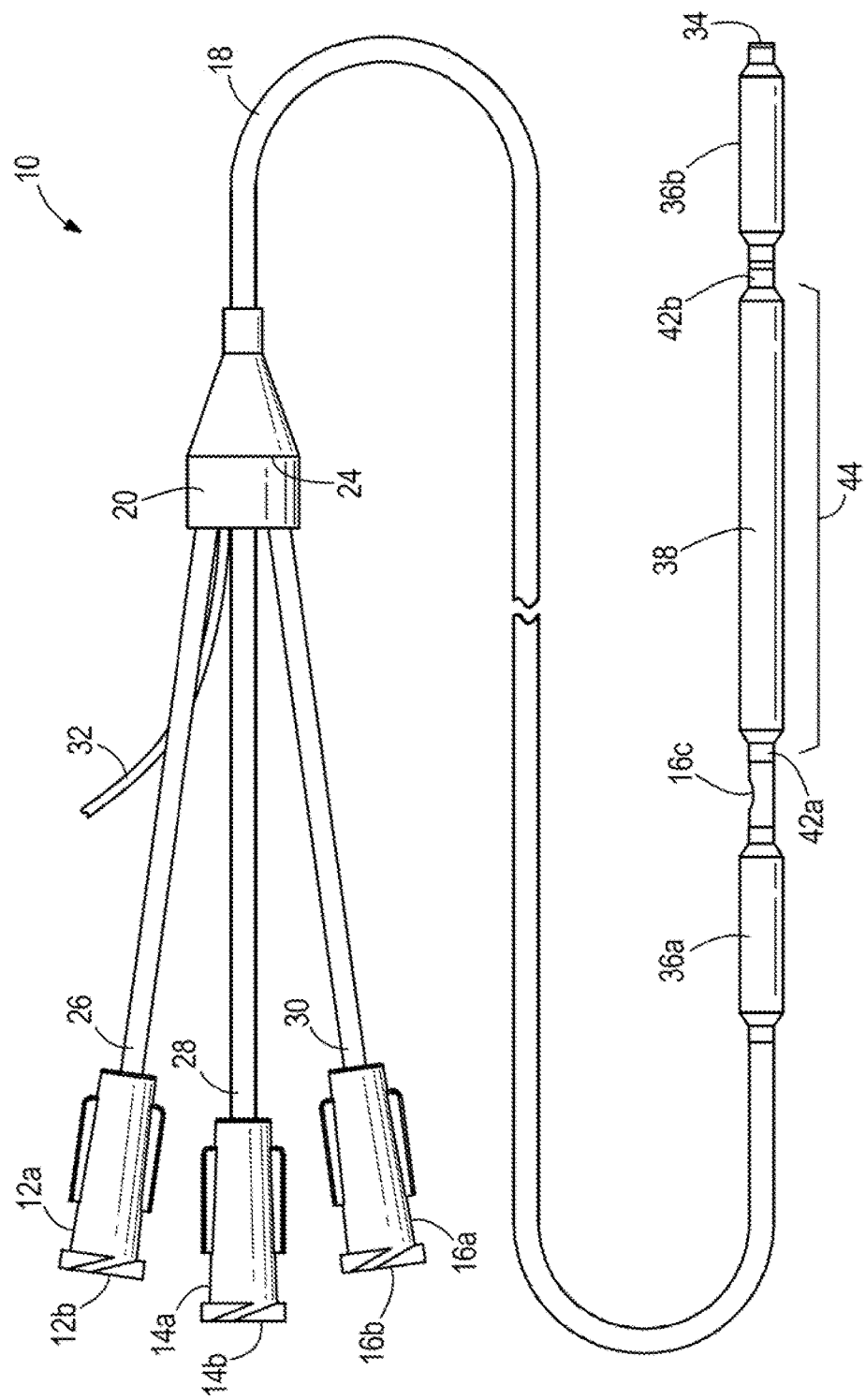
FIG. 7 illustrates one embodiment of a catheter as contemplated herein.
Figure 9:
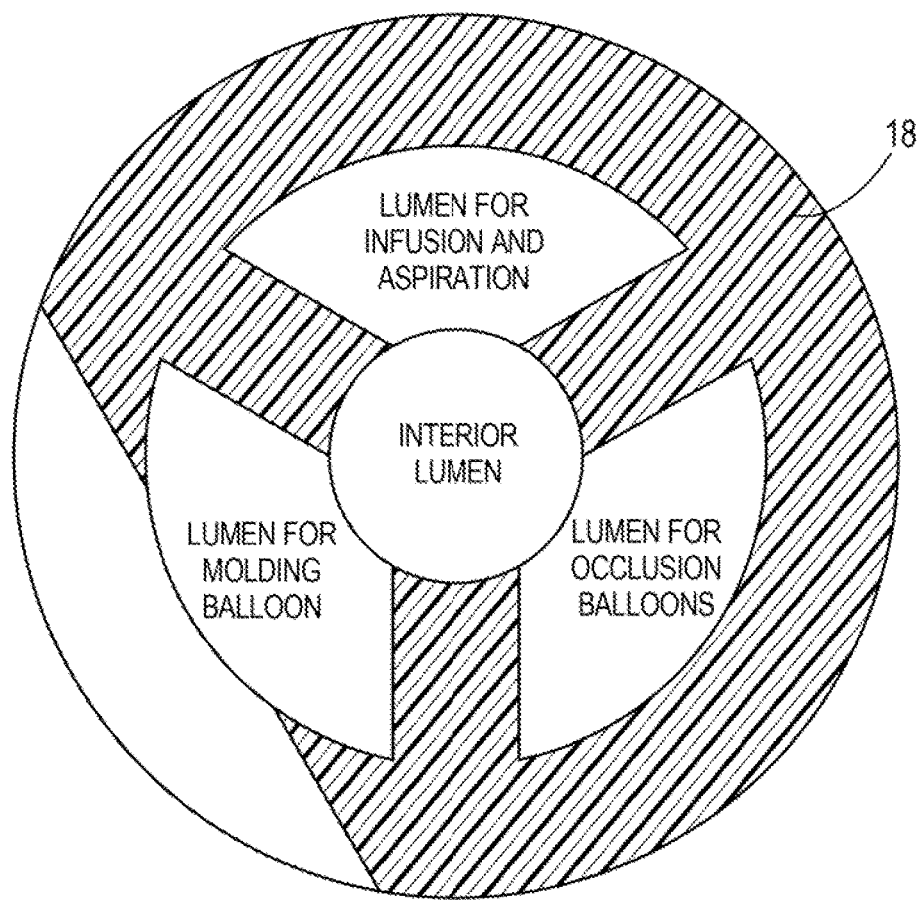
FIG. 9 illustrates a cross-section of a shaft of a catheter as contemplated herein.

Referring again to the figures, FIG. 7 illustrates a prototype of one embodiment of a catheter 10 as contemplated herein. The catheter 10 includes a catheter shaft 18. The catheter shaft includes four lumens, 12*d*, 14*d*, 16*d*, and 32*a* (FIGS. 9 and 10). Tubes 26, 28, and 30 are connected to the proximal end of the shaft to lumens 12*d*, 14*d*, and 16*d*, respectively. Lumen 12*d* is in fluid communication with occlusion balloons 36*a* and 36*b*. Lumen 14*d* is in fluid communication with molding balloon 38. Lumen 16*d* is in fluid communication with irrigation/aspiration port 16*c*. An element 32 for initiating or promoting curing of a polymer solution (e.g., a lighting element and/or a heating element) is inserted through lumen 32*a*. The tubes 26, 28, and 30 have proximal ends 12*b*, 14*b*, and 16*b*, respectively, through which fluid may be introduced and passed through the lumens 12*d*, 14*d*, and 16*d*, respectively. The tubes 26, 28, and 30 include end pieces 12*a*, 14*a*, and 16*a*, to facilitate attachment (e.g., via screwing or snapping) to a device for introducing fluid into the tubes 26, 28, and 30 and through the lumens 12*b*, 14*b*, and 16*b*, respectively. To accommodate the tubes, the proximal end of the catheter shaft 18 flares to at about point 24. The tubes are held together by a heat shrink tubing 20. The occlusion balloons 36*a*, 36*b*, and the molding balloon 38 are located at a region near a distal end 34 of the catheter. The port for irrigation/aspiration 16*c* also is located at the region near the distal end 34 of the catheter. In some embodiments, the catheter shaft 18 includes at least a portion 44 between the occlusion balloons 36*a*, 36*b* that preferably is formed of a transparent or translucent material permitting transmittance of light through this portion 44 of the catheter shaft; In further embodiments, two opaque bands 42*a*, 42*b* define the ends of the transparent/translucent portion. In even further embodiments, molding balloon 38 preferably is formed of transparent or translucent material.

Figure 8:
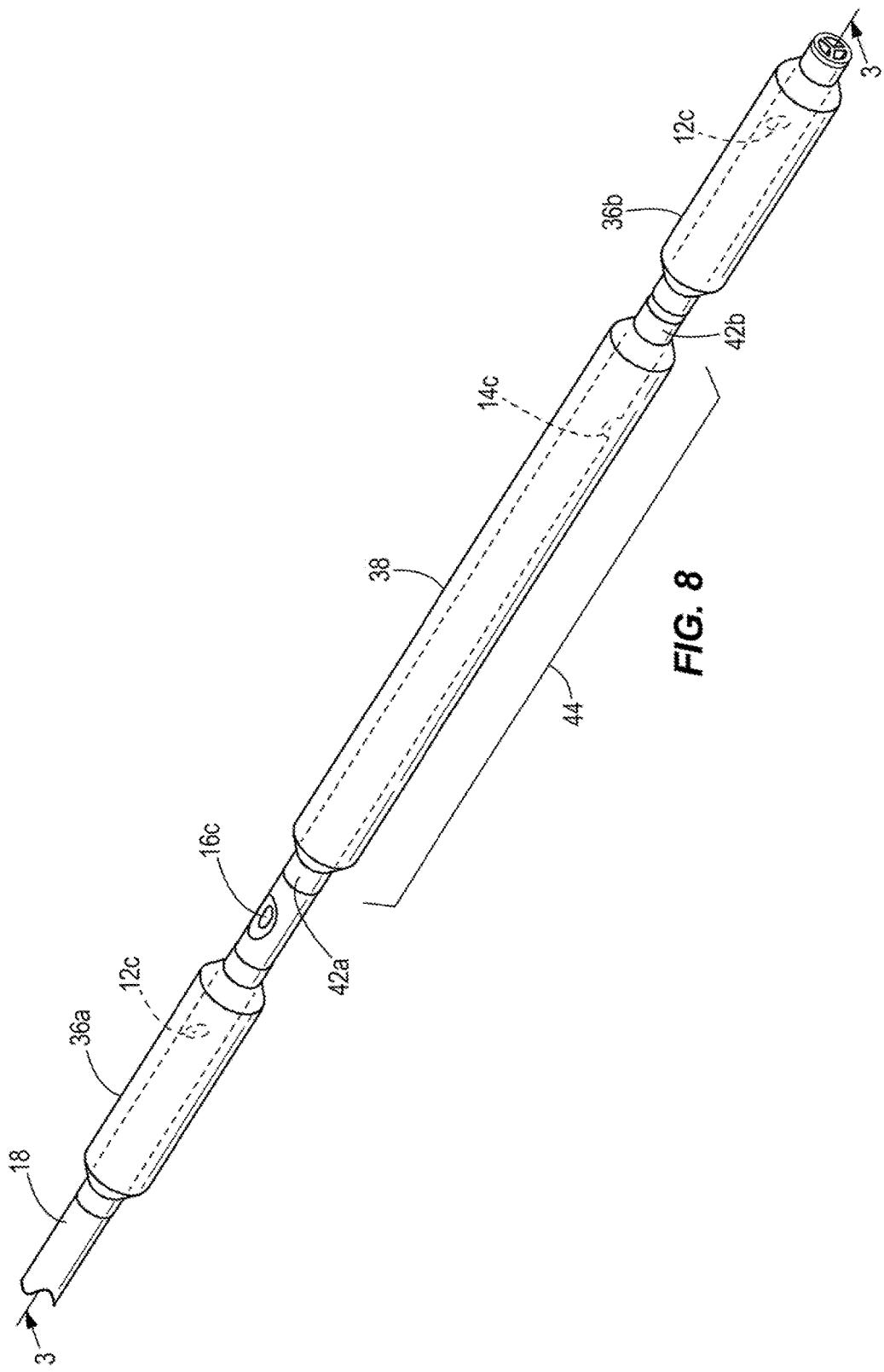
FIG. 8 illustrates one embodiment of a shaft and inflatable balloons of a catheter as contemplated herein.

Referring now to FIG. 8, shown is an enlarged view of the distal end of the catheter of FIG. 7. The shaft 18 includes ports 12*c* for inflating occlusion balloons 36*a* and 36*b* and port 14*c* for inflating molding balloon 38.

FIG. 9 illustrates a cross-section of one embodiment of the shaft 18 of a catheter as contemplated herein having four lumens. These include a lumen for the occlusion balloons, a lumen for the molding balloon, a lumen for irrigation/aspiration, and an interior lumen through, which an element for initiating or promoting curing of a prepolymer solution may be introduced (e.g., a fiber optic light source and/or a heat source).

FIG. 10 illustrates cross-section, views of the distal end of one embodiment of a shaft of a catheter as contemplated herein. At 4-4, the cross-sectional view illustrates port 12*c* for inflating occlusion balloons 36*a* and 36*b* via lumen 12*d*. At 5-5, the cross-sectional view illustrates port 16*c* for irrigating/aspirating via lumen 16*d* at an interior space in an artery provided when the occlusion balloons 36*a* and 36*b* are inflated. At 6-6, the cross-sectional view illustrates port 14*c* for inflating molding balloon 38 via lumen 14*d*. Arrows illustrate fluid flow through the respective ports.

Figure 11:
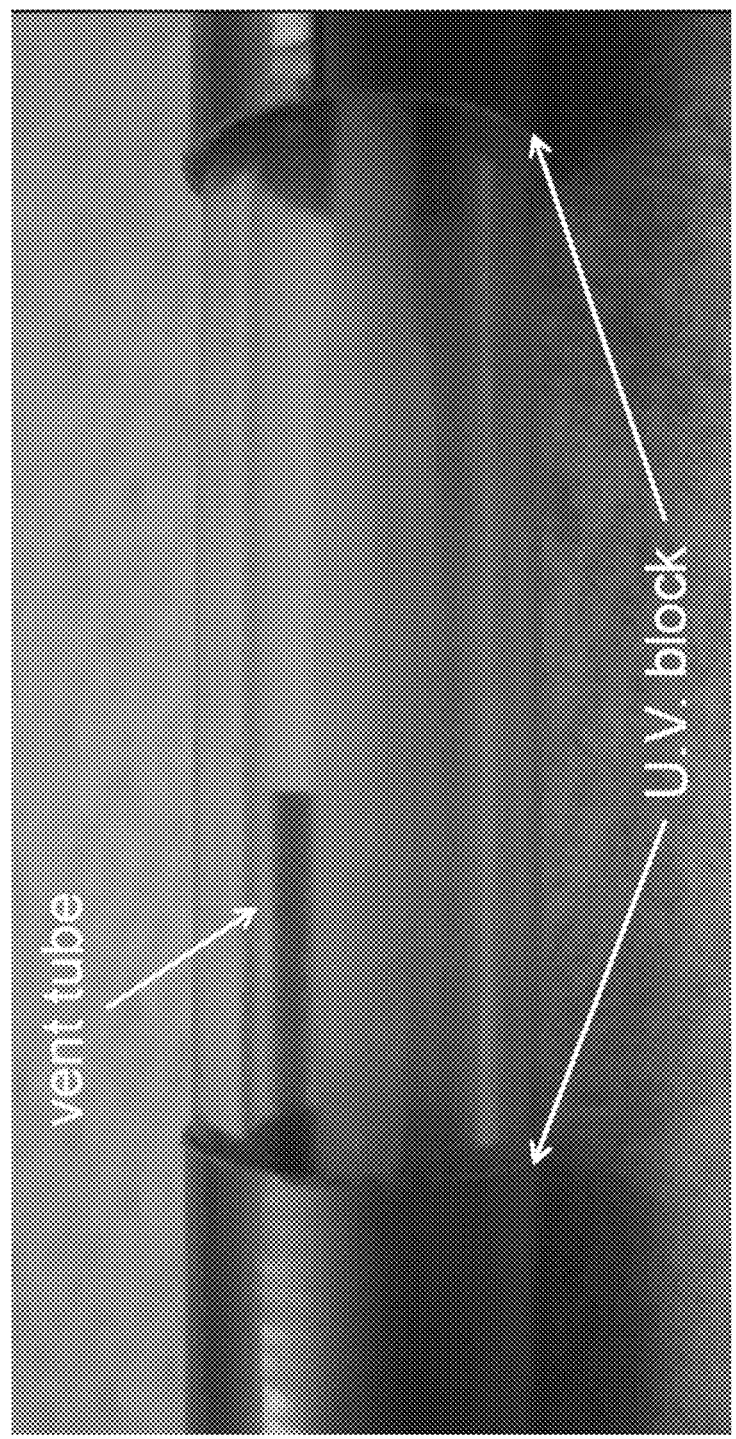
FIG. 11 illustrates blocking of UV light by the use of opaque bands.
Figure 12:
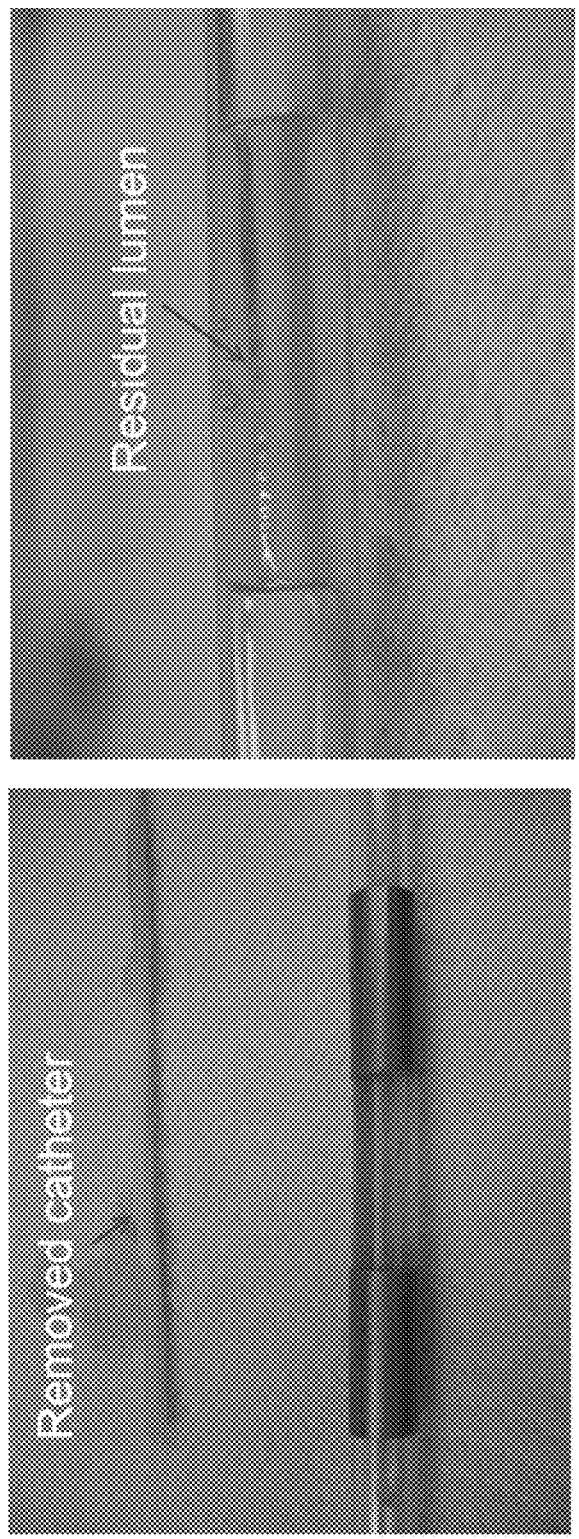
FIG. 12 illustrates a polymerized stent prepared by blocking as illustrated in FIG. 11.
Figure 13:
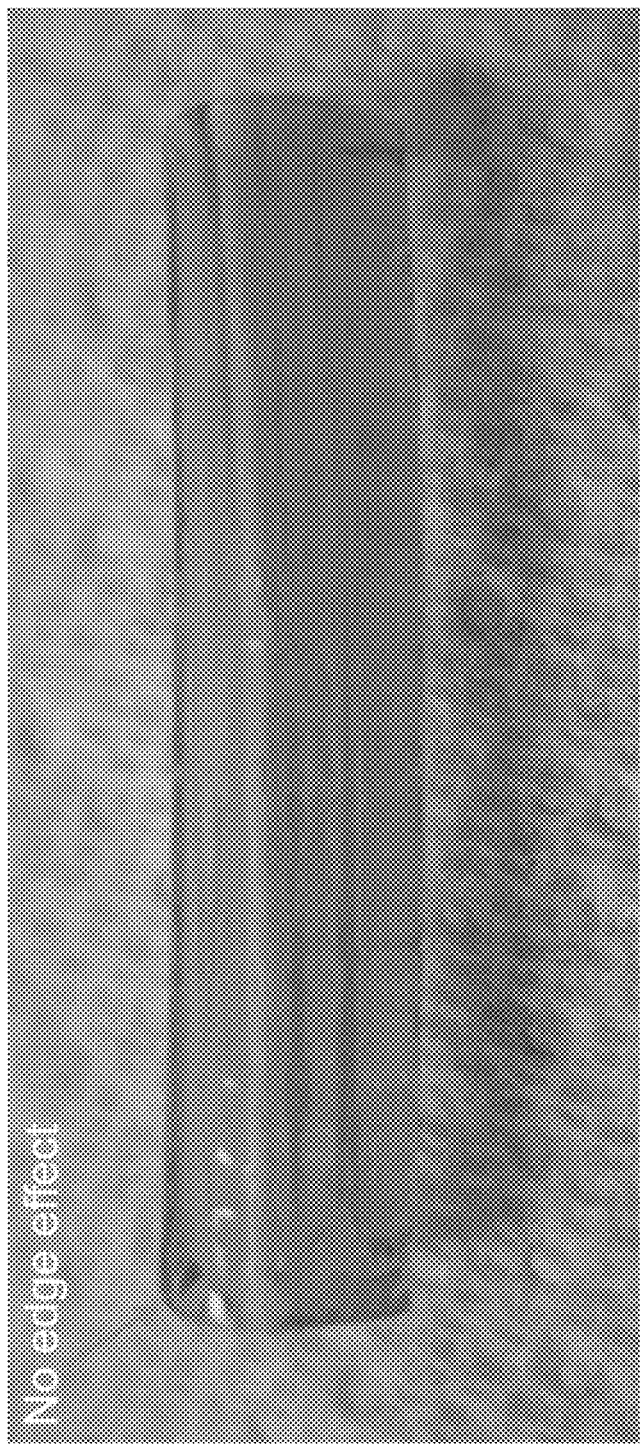
FIG. 13 illustrates that no "edge effect" is observed for a stent prepared by blocking as illustrated in FIGS. 11 and 12.

FIGS. 11-13 illustrate that blocking exposure of a prepolymer solution to UV light provides a stent lacking downwardly tinned edges. A stent was prepared in a silicon tube, and edges of the stent were defined by placing tape that blocked UV light around the silicon tube. (See FIGS. 11 and 12). The stent thereby produced lacked downwardly turned edges (i.e., no "edge effect"). (See FIG. 13).

Figure 14:
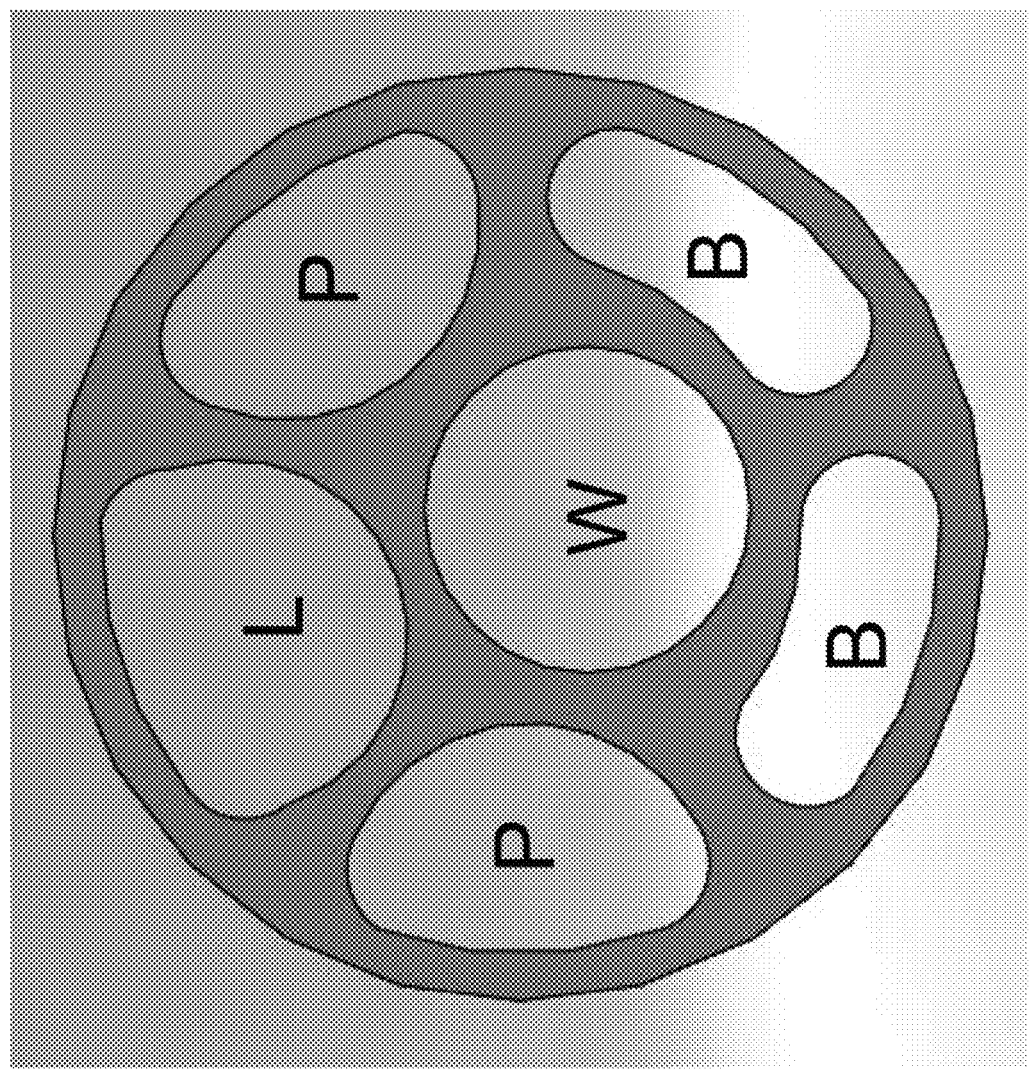
FIG. 14 illustrates a cross-sectional view of one embodiment of a catheter as contemplated herein. W—lumen for guide wire; $B_{occ}$—lumen for occlusion balloons; $B_{cast}$—lumen for casting balloon; $P_{in}$—lumen for injection; $P_{asp}$—lumen for aspiration; and L—lumen for light element.

FIG. 14 illustrates a cross-sectional view of one embodiment of a catheter device as contemplated herein. The catheter includes a central lumen for a guide wire (W) and five additional circumferential lumens for the occlusion balloons ($B_{occ}$), for the casting balloon ($B_{cast}$), for injection ($P_{in}$) (e.g., saline, polymer solution, and the like), for aspiration ($P_{asp}$) (e.g., blood, saline, polymer, and the like), and for the light element (L).

The presently disclosed catheters can be manufactured of various materials. The catheter shaft can be of any material suitable for catheters. Including, but not limited to linear low density or high density polyethylene, nylon, polyamide, polyamide copolymer, polyurethane, polypropylene, polyester copolymer, silicone rubber, or other non-thrombogenic materials. The catheter shaft with the desired number of lumens can be made by conventional extrusion processes. The distal end of the catheter shaft may include a resilient tip which comprises a material softer than that of the catheter shaft. The tip may spread or bend when it contacts body tissue, easing the catheter's passage through the vascular system and helping to avoid tissue damage. Suitable materials may include, but are not limited to ultra low density polyethylene, nylon, or polyamide copolymer. The tip can be connected to the catheter shaft by an adhesive or thermal bonding. The shaft also may include radiopaque markers, e.g., within the occlusion balloons to assist in monitoring the position of the catheter on a fluoroscope. Such markers can be provided at other locations, such as proximal to the rearmost port 12c.

The occlusion balloons and casting balloons may be made of material that includes, but is not limited to nylon, polyamide, polyamide copolymer, polyethylene, polyethylene terephthalate, polyester elastomers, polyurethane, Kraton, silicone, latex, natural rubber (e.g., Yulex brand guayule rubber), or any other soft, non-thrombogenic material which will seal against, but not expand, the arterial wall when inflated. The balloons can be tubes which expand on inflation or blow molded balloons. If the balloon material is compatible with the catheter shaft, the occlusion balloons can be attached by thermal bonding techniques, including laser bonding. An apparatus and process for laser bonding balloons onto catheters is disclosed in U.S. Pat. No. 5,267,959, which is incorporated by reference herein. An adhesive may be used, as well.

The catheter shaft and occlusion balloons may be coated with a lubricous material, such as silicone, acrylimide, or a hydrophilic polyurethane coating. The coating may facilitate passage of the catheter.

REFERENCES

1. Rosamond W, Flegal K, Friday G, Furie K, Go A, Greenlund K, Haase N, Ho M, Howard V, Kissela B, Kittner S, Lloyd-Jones D, McDermott M, Meigs J, Moy C, Nichol G, O'Donnell C J, Roger V, Rumsfeld J, Sorlie P, Steinberger J, Thom T, Wasserthiel-Smoller S, Hong Y. Heart disease and stroke statistics—2007 update: a report from the American Heart Association Statistics Committee and Stroke Statistics Subcommittee. *Circulation* 2007; 115:e69-171.
2. Smith S C, Jr., Dove X T, Jacobs A K, Kennedy J W, Kereiakes D, Kern M J, Kuntz R E, Popma J J, Schaff H V, Williams D O, Gibbons R J, Alpert J P, Eagle K A, Faxon D P, Fuster V, Gardner T J, Gregoratos G, Russell R O, Smith S C, Jr. ACC/AHA guidelines of percutaneous coronary interventions—executive summary. A report of the American College of Cardiology/American Heart Association Task Force on Practice Guidelines. *J Am Coll Cardiol* 2001; 37:2215-2239.
3. Stone G W, Ellis S G, Cox D A, Hermiller J, O'Shaughnessy C, Mann J T, Turco M, Caputo R, Bergin P, Greenberg J, Popma J J, Russell M E. A polymer-based, paclitaxel-eluting stent in patients with coronary artery disease. *N Engl J Med* 2004; 350:221-231.
4. Unger F, Serruys P W, Yacoub M H, Ilsiey C, Paulsen P K, Nielsen T T, Eysmann L, Kiemeneij F. Revascularization in multivessel disease: comparison between two-year outcomes of coronary bypass surgery and stenting. *J Thorac Cardiovasc Surg* 2003; 125:809-820.
5. Lagerqvist B, James S K, Stenestrand U, Lindback J, Nilsson T, Wallentin L. Long-term outcomes with drug-eluting stents versus bare-metal stents in Sweden. *N Engl J Med* 2007; 356:1009-1019.
6. Spaulding C, Daemen J, Boersma E, Cutlip D E, Serruys P W. A pooled analysis of data comparing sirolimus-eluting stents with bare-metal stents. *N Engl J Med* 2007; 356:989-997.
7. Boden W E, O'Rourke R A, Teo K K, Hartigan P M, Maron D J, Kostuk W J, Knudtson M, Dada M, Casperson P, Harris C L, Chaitman B R, Shaw L, Gosselin G, Nawaz S, Title L M, Gau G, Blaustein A S, Booth D C, Bates E R, Spertus J A, Berman D S, Mancini G B, Weintraub W S. Optimal medical therapy with or without PCI for stable coronary disease. *N Engl J Med* 2007; 356:1503-1516.
8. Clowes A W, Reidy M A, Clowes M M. Mechanisms of stenosis after arterial injury. *Lab Invest* 1983; 49:208-215.
9. Fingerle J, Johnson R, Clowes A W, Majesky M W, Reidy M A. Role of platelets in smooth muscle cell proliferation and migration after vascular injury in rat carotid artery. *Proc Natl Acad Sci USA* 1989; 86:8412-8416.
10. Davies M G, Hagen P O. Pathobiology of intimal hyperplasia. *Br J Surg* 1994; 81:1254-1269.
11. Libby P, Schwartz D, Brogi E, Tanaka H, Clinton S K. A cascade model for restenosis. A special case of atherosclerosis progression. *Circulation* 1992; 86:11147-11152.
12. Lindner V, Lappi D A, Baird A, Majack R A, Reidy M A. Role of bask fibroblast growth factor in vascular lesion formation. *Circ Res* 1991; 68:106-113.
13. Douglas S A, Louden C, Vickery-Clark L M, Storer B L, Hart T, Feuerstein G Z, Elliott J D, Ohlstein E H. A role for endogenous endothelin-1 in neointimal formation after rat carotid artery balloon angioplasty. Protective effects of the novel nonpeptide endothelin receptor antagonist SB 209670. *Circ Res* 1994; 75:190-197.
14. Prescott M F, Webb R L, Reidy M A. Angiotensin-converting enzyme inhibitor versus angiotensin II, AT1 receptor antagonist. Effects on smooth muscle cell migration and proliferation after balloon catheter injury. *Am J Pathol* 1991; 139:1291-1296.
15. Lindner V, Majack R A, Reidy M A. Basic fibroblast growth factor stimulates endothelial regrowth and proliferation in denuded arteries. *J Clin Invest* 1990; 85:2004-2008.
16. Nabel E G, Shum L, Pompili V J, Yang Z Y, San H, Shu H B, Liptay S, Gold L, Gordon D, Derynck R. Direct transfer of transforming growth factor beta 1 gene into arteries stimulates fibrocellular hyperplasia. *Proc Natl Acad Sci USA* 1993; 90:10759-10763.
17. Majesky M W, Lindner V, Twardzik D R, Schwartz S M, Reidy M A. Production of transforming growth factor beta 1 during repair of arterial injury. *J Clin Invest* 1991; 88:904-910.

18. Kibbe M, Billiar T, Tzeng E. Inducible nitric oxide synthase and vascular injury. *Cardiovasc Res* 1999; 43:650-657.
19. Vaughn M W, Kuo L, Liao J C. Estimation of nitric oxide production and reaction rates in tissue by use of a mathematical model. *Am J Physiol* 1998; 274:H2163-H2176.
20. Radomski M W, Palmer R M, Moncada S. Endogenous nitric oxide inhibits human platelet adhesion to vascular endothelium. *Lancet* 1987; 2:1057-1058.
21. Kubes P, Suzuki M, Granger D N. Nitric oxide: an endogenous modulator of leukocyte adhesion. *Proc Natl Acad Sci USA* 1991; 88:4651-4655.
22. Kibbe M R, Li J, Nie S, Watkins S C, Lizonova A, Kovesdi I, Simmons R L, Billiar T R, Tzeng E. Inducible nitric oxide synthase (iNOS) expression upregulates p21 and inhibits vascular smooth muscle cell proliferation through p42/44 mitogen-activated protein kinase activation and independent of p53 and cyclic guanosine monophosphate [In Process Citation]. *J Vasc Surg* 2000; 31:1214-1228.
23. Garg U C, Hassid A. Nitric oxide-generating vasodilators and 8-bromo-cyclic guanosine monophosphate inhibit mitogenesis and proliferation of cultured rat vascular smooth muscle cells. *J Clin Invest* 1989; 83:1774-1777.
24. Nishio E. Fukushima K, Shiozaki M, Watanabe Y. Nitric oxide donor SNAP induces apoptosis in smooth muscle cells through cGMP-independent mechanism. *Biochem Biophys Res Commun* 1996; 221:163-168.
25. Tzeng E, Kim Y M, Pitt B R, Lizonova A, Kovesdi I, Billiar T R. Adenoviral transfer of the inducible nitric oxide synthase gene blocks endothelial cell apoptosis. *Surgery* 1997; 122:255-263.
26. Ignarro L J, Buga G M, Wood K S, Byrns R E, Chaudhuri G. Endothelium-derived relaxing factor produced and released from artery and vein is nitric oxide. *Proc Natl Acad Sci USA* 1987; 84:9265-9269.
27. Furchgott R F, Zawadzki J V. The obligatory role of endothelial cells in the relaxation of arterial smooth muscle by acetylcholine. *Nature* 1980; 288:373-376.
28. Davies M G, Daleo H, Kim J H, Barber L, Svendsen E, Hagen P O. Control of accelerated vein graft atheroma with the nitric oxide precursor: L-arginine. *J Surg Res* 1995; 59:35-42.
29. Marks D S, Vita J A, Folts J D, Keaney J F J, Welch G N, Loscalzo J. Inhibition of neointimal proliferation in rabbits after vascular injury by a single treatment with a protein adduct of nitric oxide. *J Clin Invest* 1995; 96:2630-2638.
30. Lee J S, Adrie C, Jacob H J, Roberts J D J, Zapol W M, Bloch K D. Chronic inhalation of nitric oxide inhibits neointimal formation after balloon-induced arterial injury. *Circ Res* 1996; 78:337-342.
31. Kaul S, Cercek B, Rengstrom J, Xu X P, Molloy M D, Dimaynga P, Parikh A K, Fishbein M C, Nilsson J, Rajavashisth T B, Shah P K. Polymeric-based perivascular delivery of a nitric oxide donor inhibits intimal thickening after balloon denudation arterial injury: role of nuclear factor-kappaB. *J Am Coil Cardiol* 2000; 35:493-501.
32. von der Leyen H, Gibbons G H, Morishita R, Lewis N P, Zhang L, Nakajima M, Kaneda Y, Cooke J P, Dzau V J. Gene therapy inhibiting neointimal vascular lesion: in vivo transfer of endothelial cell nitric oxide synthase gene. *Proc Natl Acad Sci USA* 1995; 92:1137-1141.
33. Shears L L, Kibbe M R, Murdock A D, Billiar T R, Lizonova A, Kovesdi I, Watkins S C, Tzeng E. Efficient inhibition of intimal hyperplasia by adenovirus-mediated inducible nitric oxide synthase gene transfer to rats and pigs in vivo. *Journal of the American College of Surgeons* 1998; 187:295-306.
34. Kibbe M R, Tzeng E, Gleixner S L, Watkins S C, Kovesdi I, Lizonova A, Makaroun M S, Billiar T R, Rhee R Y. Adenovirus-mediated gene transfer of human inducible nitric oxide synthase in porcine vein grafts inhibits intimal hyperplasia. *J Vasc Surg* 2001; 34:156-165.
35. Bohl K S, West J L. Nitric oxide-generating polymers reduce platelet adhesion and smooth muscle cell proliferation. *Biomaterials* 2000; 21:2273-2278.
36. Kown M B, Yamaguchi A, Jahncke C L, Miniati D, Murata S, Grunenfelder J, Koransky M L, Rothbard J B, Robhins R C. L-arginine polymers inhibit the development of vein graft neointimal hyperplasia. *J Thorac Cardiovasc Surg* 2001; 121:971-980.
37. Chaux A, Ruan X M, Fishbein M C, Ouyang Y, Kaul S, Pass J A, Matloff J M. Perivascular delivery of a nitric oxide donor inhibits neointimal hyperplasia in vein grafts implanted in the arterial circulation. *J Thorac Cardiovasc Surg* 1998; 115:604-612.
38. Fleser P S, Nuthakki V K, Malinzak L E, Callahan R E, Seymour M L, Reynolds M M, Merz S I, Meyerhoff M E, Bendick P J, Zelenock G B, Shanley C J. Nitric oxide-releasing biopolymers inhibit thrombus formation in a sheep model of arteriovenous bridge grafts. *J Vasc Surg* 2004; 40:803-811.
39. Pearce C G, Najjar S F, Kapadia M R, Murar J, Eng J, Lyle B, Aalami O O, Jiang Q, Hrabie J A, Saavedra J E, Keefer L K, Kibbe M R. Beneficial effect of a short-acting NO donor for the prevention of neointimal hyperplasia. *Free Radic Biol Med* 2008; 44:73-81.
40. Kapadia M R, Chow L W, Tsihlis N D, Ahanchi S S, Eng J W, Murar J, Martinez J, Popowich D A, Jiang Q, Hrabie J A, Saavedra I E, Keefer L K, Hulvat J F, Stupp S I, Kibbe M R. Nitric oxide and nanotechnology; a novel approach to inhibit neointimal hyperplasia. *J Vasc Surg* 2008; 47:173-182.
41. Fishbein I, Alferiev I, Bakay M, Stachelek S J, Sobolewski P, Lai M, Choi E, Chen I W, Levy R J. Local delivery of gene vectors from bare-metal stents by use of a biodegradable synthetic complex inhibits in-stent restenosis in rat carotid arteries. *Circulation* 2008; 117:2096-2103.
42. Hrabie J A, Keefer L K. Chemistry of the nitric oxide-releasing diazeniumdiolate ("nitrosohydroxylamine") functional group and its oxygen-substituted derivatives. *Chem Rev* 2002; 102:1135-1154.
43. Yoon J H, Wu C J, Homme J, Tuch R J, Wolff R G, Topol E J, Lincoff A M. Local delivery of nitric oxide from an eluting stent to inhibit neointimal thickening in a porcine coronary injury model. *Yonsei Med J* 2002; 43:242-251.
44. Hou D, Narciso H, Kamdar K, Zhang P, Barclay B, March K L, Stent-based nitric oxide delivery reducing neointimal proliferation in a porcine carotid overstretch injury model. *Cardiovasc Intervent Radiol* 2005; 28:60-65.
45. Zhang E, Annich G M, Miskulin J, Osterholzer K, Merz S I, Bartlett R H, Meyerhoff M E. Nitric oxide releasing silicone rubbers with improved blood compatibility: preparation, characterization, and in vivo evaluation. *Biomaterials* 2002; 23:1485-1494.
46. Frost M C, Rudich S M, Zhang H, Maraschio M A, Meyerhoff M E. In vivo biocompatibility and analytical performance of intravascular amperometric oxygen sensors prepared with improved nitric oxide-releasing silicone rubber coating. *Anal Chem* 2002; 74:5942-5947.
47. Smith D J, Chakravarthy D, Pulfer S, Simmons M L, Hrabie J A, Citro M L, Saavedra J E, Davies K M, Hutsell T C, Mooradian D L, Hanson S R, Keefer L K. Nitric oxide-releasing polymers containing the [N(O)NO]—group. *J Med Chem* 1996; 39:1148-1156.
48. Pulfer S K, Ott D, Smith D J. Incorporation of nitric oxide-releasing crosslinked polyethyleneimine microspheres into vascular grafts. *J Biomed Mater Res* 1997; 37:182-189.
49. Iakovou I, Schmidt T, Bonizzoni E, Ge L, Sangiorgi G M, Stankovic G, Airoldi F, Chieffo A, Montorfano M, Carlino M, Michev I, Corvaja N, Briguori C, Gerckens U, Grube E, Colombo A. Incidence, predictors, and outcome of thrombosis after successful implantation of drug-eluting stents. *JAMA* 2005; 293:2126-2130.
50. Spaulding C, Daemen J, Boersma E, Cutlip D E, Serruys P W. A pooled analysis of data comparing sirolimus-eluting stents with bare-metal stents. *N Engl J Med* 2007; 356:989-997.
51. Lagerqvist B, James S K, Stenestrand U, Lindback J, Nilsson T, Wallentin L. Long-term outcomes with drug-eluting stents versus bare-metal stents in Sweden. *N Engl J Med* 2007; 356:1009-1019.
52. Maisel W H. Unanswered questions—drug-eluting stents and the risk of late thrombosis. *N Engl J Med* 2007; 356:981-984.
53. Finn A V, Joner M, Nakazawa G, Kolodgie F, Newell J, John M C, Gold H K, Virmani R. Pathological correlates of late drug-eluting stent thrombosis: strut coverage as a marker of endothelialization. *Circulation* 2007; 115:2435-2441.
54. Stack R S, Califf R M, Phillips H R, Pryor D B, Quigley P J, Bauman R P, Tcheng J E, Greenfield J C, Jr. interventional cardiac catheterization at Duke Medical Center. *Am J Cardiol* 1988; 62:3F-24F.
55. Tamai H, Igaki K, Kyo E, Kosuga K, Kawashima A, Matsui S, Komori H, Tsuji T, Motohara S, Uehata H. Initial and 6-month results of biodegradable poly-1-actic acid coronary stents in humans. *Circulation* 2000; 102:399-404.
56. Commandeur S, van Beusekom H M, van der Giessen W J. Polymers, drug release, and drug-eluting stents. *J Interv Cardiol* 2006; 19:500-506.
57. van der Giessen W J, Lineoff A M, Schwartz R S, van Beusekom H M, Serruys P W, Holmes D R, Jr., Ellis S G, Topol E J. Marked inflammatory sequelae to implantation of biodegradable and nonbiodegradable polymers in porcine coronary arteries. *Circulation* 1996; 94:1690-1697.
58. Yang J, Webb A R, Pickerill S J, Hageman G, Ameer G A. Synthesis and evaluation of poly(diol citrate) biodegradable elastomers. *Biomaterials* 2006; 27:1889-1898.
59. Yang J, Motlagh D, Webb A R, Ameer G A. Novel biphasic elastomeric scaffold for small-diameter blood vessel tissue engineering. *Tissue Eng* 2005; 11:1876-1886.
60. Yang J, Motlagh D, Allen J B, Webb A R, Kibbe M R, Aalami O, Kapadia M, Carroll T J, Ameer G A. Modulating Expanded Polytetrafluoroethylene Vascular Graft Host Response via Citric Acid-Based Biodegradable Elastomers. *Adv Mater* 2006; 18:1493-1498.
61. Motlagh D, Yang J, Lui K Y, Webb A R, Ameer G A. Hemocompatibility evaluation of poly(glycerol-sebacate) in vitro for vascular tissue engineering. *Biomaterials* 2006; 27:4315-4324.
62. Tamada Y, Kulik E A, Ikada Y. Simple method for platelet counting. *Biomaterials* 1995; 16:259-261.
63. Anseth K S, Metters A T, Bryant S J, Martens P J, Elisseeff J H, Bowman C N. In situ forming degradable networks and their application in tissue engineering and drug delivery. *J Control Release* 2002; 78:199-209.
64. Burdick J A, Peterson A J, Anseth K S. Conversion and temperature profiles during the photoinitiated polymerization of thick orthopaedic biomaterials. *Biomaterials* 2001; 22:1779-1786.
65. Rydholm A E, Bowman C N, Anseth K S. Degradable thiol-aerylate photopolymers: polymerization and degradation behavior of an in situ forming biomaterial. *Biomaterials* 2005; 26:4495-4506.
66. Simms H M, Bowman C M, Anseth K S. Using living radical polymerization to enable facile incorporation of materials in microfluidic cell culture devices. *Biomaterials* 2008; 29:2228-2236.
67. Reisman M, Shaman B J, Harms V. Analysis of heat generation during rotational atherectomy using different operational techniques. *Cather Cardiovasc Diagn* 1998; 44:453-455.
68. Yang J, Motlagh D, Webb A R, Ameer G A. Novel biphasic elastomeric scaffold for small-diameter blood vessel tissue engineering. *Tissue Eng* 2005; 11:1876-1886.
69. Dyet J F, Watts W G, Ettles D F, Nicholson A A. Mechanical properties of metallic stents: how do these properties influence the choice of stent for specific lesions? *Cardiovasc Intervent Radiol* 2000; 23:47-54.
70. Nikanorov A, Smouse H B, Osman K, Bialas M, Shrivastava S, Schwartz L B. Fracture of self-expanding nitinol stents stressed in vitro under simulated intravascular conditions. *J Vasc Surg* 2008; 48:435-440.
71. Chen M C, Tsai H W, Chang Y, Lai W Y, Mi F L, Liu C T, Wong H S, Sung H W. Rapidly self-expandable polymeric stents with a shape-memory property. *Biomacromolecules* 2007; 8:2774-2780.
72. Kibbe M R, Nie S, Yoneyama T, Hatakeyama K, Lizonova A, Kovesdi L Billiar T R, Tzeng E. Optimization of ex vivo inducible nitric oxide synthase gene transfer to vein grafts. *Surgery* 1999; 126:323-329.
73. Webb A R, Macrie B D, Ray A S, Russo J E, Siegel A M, Glucksberg M R, Ameer G A. In vitro characterization of a compliant biodegradable scaffold with a novel bioreactor system. *Ann Biomed Eng* 2007; 35:1357-1367.
74. Gunther S, Alexander R W, Atkinson W J, Gimbrone M A. Functional angiotensin-Ii receptors in cultured vascular smooth-muscle cells. *J Cell Biol* 1982; 92:289-298.
75. Mahabaleshwar G H, Somanath P R, Byzova T V, Methods for Isolation of Endothelial and Smooth Muscle Cells and In Vitro Proliferation Assays. In: *Cardiovascular Disease, Volume* 2: *Molecular Medicine.* 2006:197-208.
76. Allen J, Khan S, Serrano M C, Ameer G. Characterization of Porcine Circulating Progenitor Cells: Toward a Functional Endothelium, Tissue Eng 2008.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. The cited patent and non-patent references are incorporated by reference in their entireties. The definitions provided in the present specification supersede any definition for a term provided in a cited reference.

I claim:

1. A catheter for forming a liquid cast stent in an artery, the catheter comprising:
   (a) a catheter shaft comprising a proximal end and a distal end;
   (b) a proximal occlusion balloon;
   (c) a distal occlusion balloon;
   (d) an inflation lumen in fluid communication with the proximal occlusion balloon and the proximal end of the catheter shaft and in fluid communication with the distal occlusion balloon and the proximal end of the catheter shaft, wherein after the catheter is inserted and subsequently the proximal occlusion balloon and distal occlusion balloon are inflated, an interior space between the inflated proximal occlusion balloon and the inflated distal occlusion balloon is formed;
   (e) a middle balloon between the proximal occlusion balloon and the distal occlusion balloon, wherein the middle balloon is formed from material that is transparent or translucent and that permits transmission of light from the element to the interior space between the inflated proximal occlusion balloon and the inflated distal occlusion balloon;
   (f) an inflation lumen in fluid communication with the middle balloon and the proximal end of the catheter shaft;
   (g) at least one infusion/aspiration port between the proximal occlusion balloon and the distal occlusion balloon and an infusion/aspiration lumen for delivering/removing a liquid to or from the infusion/aspiration port, the at least one infusion/aspiration lumen in fluid communication with the proximal end of the catheter shaft; and
   (h) an element that when activated initiates or promotes curing of a polymer solution administered in the interior space between the inflated proximal occlusion balloon and the inflated distal occlusion balloon, wherein the element delivers light;
wherein at least a portion of the catheter shaft is transparent or translucent and the transparent or translucent portion is located between the proximal occlusion balloon and the distal occlusion balloon within the middle balloon, the catheter further comprising opaque bands that define a proximal end and a distal end of the transparent or translucent portion, wherein when the middle balloon is inflated, the middle balloon overlaps the opaque bands and the element delivers light through the transparent or translucent portion of the catheter shaft and through the middle balloon to initiate or promote curing of the polymer solution to form a stent that does not include downwardly turned edges.

2. The catheter of claim 1, wherein the element delivers visible light.

3. The catheter of claim 1, wherein the element delivers UV light.

4. The catheter of claim 1, wherein the element delivers light having a wavelength of about 300-500 nm.

5. The catheter of claim 1, wherein the element delivers light having an intensity of at least about 10 mW/cm$^2$.

6. The catheter of claim 1, wherein the element is a fiber optic element, a laser element, or a light emitting diode (LED) element.

7. The catheter of claim 1, wherein component (d) comprises an inflation lumen in fluid communication with the proximal occlusion balloon and the proximal end of the catheter shaft and a separate inflation lumen in fluid communication with the distal occlusion balloon and the proximal end of the catheter shaft, wherein the proximal occlusion balloon and the distal occlusion balloon can be inflated separately.

8. The catheter of claim 1, wherein component (d) consists of a single lumen in fluid communication with the proximal end of the catheter shaft and both of the proximal occlusion balloon and the distal occlusion balloon, wherein the single lumen can be utilized to inflate both of the proximal occlusion balloon and the distal occlusion balloon.

9. The catheter of claim 1, comprising at least one separate infusion port and at least one separate aspiration port.

10. The catheter of claim 1, wherein component (d) comprises an inflation lumen in fluid communication with the proximal occlusion balloon and the proximal end of the catheter shaft and a separate inflation lumen in fluid communication with the distal occlusion balloon and the proximal end of the catheter shaft, wherein the proximal occlusion balloon and the distal occlusion balloon can be inflated separately.

11. The catheter of claim 1, wherein component (d) consists of a single lumen in fluid communication with the proximal end of the catheter shaft and both of the proximal occlusion balloon and the distal occlusion balloon, wherein the single lumen can be utilized to inflate both of the proximal occlusion balloon and the distal occlusion balloon.

12. The catheter of claim 1, comprising at least one separate infusion port and at least one separate aspiration port.

* * * * *

UNITED STATES PATENT AND TRADEMARK OFFICE
CERTIFICATE OF CORRECTION

PATENT NO. : 10,398,806 B2
APPLICATION NO. : 13/652058
DATED : September 3, 2019
INVENTOR(S) : Melina R. Kibbe It is certified that error appears in the above-identified patent and that said Letters Patent is hereby corrected as shown below:

On the Title Page

In The (57) Abstract:
Line 2, "stents, typically" should be --stents. Typically--.

In the Specification

Column 2, Line 39, "m inflation" should be --an inflation--.

Column 2, Line 63, "infusion/aspiration" should be --infusion)/aspiration--.

Column 3, Line 11, "Alter" should be --After--.

Column 3, Line 18, "axe" should be --are--.

Column 3, Line 25, "solution via" should be --solution (e.g., via--.

Column 3, Line 32, "light), in" should be --light). In--.

Column 4, Line 22, "tire" should be --the--.

Column 5, Line 38, "pins" should be --plus--.

Column 5, Line 50, "neointimai" should be --neointimal--.

Column 7, Line 6, "nm-400" should be --nm-100--.

Column 7, Line 32, "minute), in" should be --minute). In--.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,398,806 B2

Column 7, Line 41, "5,554,092" should be --5,514,092--.

Column 7, Line 60, "neointimai" should be --neointimal--.

Column 8, Line 7, "neointimai" should be --neointimal--.

Column 9, Line 12, "she" should be --site--.

Column 9, Line 59, "neointimai" should be --neointimal--.

Column 10, Lines 60-61, "poly-ethylene amide)" should be --poly(ethylene amide)--.

Column 12, Line 4, "ceil" should be --cell--.

Column 12, Line 25, "Tire" should be --The--.

Column 13, Line 60, "die" should be --the--.

Column 14, Line 52, "insetting" should be --inserting--.

Column 15, Line 18, "stem" should be --stent--.

Column 15, Line 36, "Tor" should be --For--.

Column 15, Line 64, "now-reacted" should be --non-reacted--.

Column 16, Line 4, "polymerization, in" should be --polymerization. In--.

Column 16, Lines 39-40, "proliferation), ideally," should be --proliferation). Ideally--.

Column 17, Line 67, "solution), in" should be --solution). In--.

Column 18, Line 63, "tinned" should be --turned--.

Column 19, Line 11, "catheters. Including" should be --catheters, including--.

Column 19, Line 56, "Thorn" should be --Thom--.

Column 21, Line 41, "Daleo" should be --Dalen--.

Column 21, Line 55, "Dimaynga" should be --Dimayuga--.

Column 21, Line 59, "Coil" should be --Coll--.

Column 22, Line 16, "Robhins" should be --Robbins--.

CERTIFICATE OF CORRECTION (continued)
U.S. Pat. No. 10,398,806 B2

Column 23, Line 41, "poly-l-actic" should be --poly-l-lactic--.

Column 24, Line 21, "Cather" should be --Cathet--.